US009513358B2

(12) United States Patent
Levin

(10) Patent No.: US 9,513,358 B2
(45) Date of Patent: Dec. 6, 2016

(54) METHOD AND APPARATUS FOR MAGNETIC RESONANCE IMAGING

(71) Applicant: Pavel Levin, Brooklyn, NY (US)

(72) Inventor: Pavel Levin, Brooklyn, NY (US)

(73) Assignee: Vaposun Inc., Brooklyn, NY (US)

( * ) Notice: Subject to any disclaimer, the term of this patent is extended or adjusted under 35 U.S.C. 154(b) by 506 days.

(21) Appl. No.: 14/205,507

(22) Filed: Mar. 12, 2014

(65) Prior Publication Data

US 2014/0266195 A1    Sep. 18, 2014

Related U.S. Application Data

(60) Provisional application No. 61/777,174, filed on Mar. 12, 2013.

(51) Int. Cl.
| | | |
|---|---|---|
| *G01N 24/08* | (2006.01) | |
| *G01R 33/56* | (2006.01) | |
| *G01R 33/565* | (2006.01) | |
| G01R 33/563 | (2006.01) | |

(52) U.S. Cl.
CPC ..... *G01R 33/56509* (2013.01); *G01R 33/5602* (2013.01); *G01N 24/081* (2013.01); *G01N 24/084* (2013.01); *G01R 33/56341* (2013.01); *G01R 33/56366* (2013.01)

(58) Field of Classification Search
CPC ............ G01R 33/56509; G01R 33/5602; G01R 33/56341; G01R 33/56366; G01N 24/084; G01N 24/081

See application file for complete search history.

(56) References Cited

U.S. PATENT DOCUMENTS

| | | | | |
|---|---|---|---|---|
| 5,492,123 | A | * | 2/1996 | Edelman .......... G01R 33/56341 600/410 |
| 6,614,225 | B1 | * | 9/2003 | Feinberg ............ G01R 33/4835 324/307 |
| 6,842,000 | B2 | | 1/2005 | Norris |
| 7,310,548 | B2 | | 12/2007 | Van Den Brink |
| 7,514,927 | B2 | | 4/2009 | Herzka |
| 8,076,936 | B2 | | 12/2011 | Borthakur |
| 2011/0254548 | A1 | | 10/2011 | Setsompop |

OTHER PUBLICATIONS

E.O. Stejskal, J.E. Tanner, Spin-diffusion measurements: spin echoes in the presence of a time-dependent field gradient, J.Chem. Phys., vol. 42, 1965, p. 288-292 (US).

J.A. McNab and K.L. Miller, Steady-state diffusion-weighted imaging: theory, acquisition and analysis, NMR Biomed., vol. 23, 2010, p. 781-793 (US).

(Continued)

*Primary Examiner* — G. M. Hyder

(57) ABSTRACT

The method and system for correcting motion-induced phase errors in Magnetic Resonance Imaging (MRI) use a phase shift of the non-phase encoded reference echo-signal accumulated during the diffusion-weighting in order to characterize bulk motion and tissue deformation and to compensate their effect for correcting the diffusion/perfusion-weighted image. The sequences unbalanced with respect to the first motion derivative are used for distinguishing the perfusion component. The MRI apparatus provides additional excitation resonance-frequency ranges for forming the reference echo signals.

20 Claims, 9 Drawing Sheets

(56) References Cited

OTHER PUBLICATIONS

A.M. Ulug et al., Correction of motional artifacts in diffusion-weighted images using a reference phase map, Magnetic Resonance in Medicine, vol. 34, No. 2, 1995, pp. 476-480 (US).

G.K. Rohde et al., Comprehensive Approach for Correction of Motion and Distortion in Diffusion-Weighted MRI, Magnetic Resonance in Medicine, vol. 51, No. 1, 2004, pp. 103-114 (US).

* cited by examiner

METHOD AND APPARATUS FOR MAGNETIC RESONANCE IMAGING

CROSS-REFERENCE TO RELATED APPLICATIONS

This patent application claims the benefit of priority, under 35 U.S.C. Section 119(e), U.S. Provisional patent application No. 61/777,174 "Method and apparatus for diffusion-weighted magnetic resonance imaging" to Pavel Levin, filed on 2013 Mar. 12.

STATEMENT REGARDING FEDERALLY SPONSORED RESEARCH OR DEVELOPMENT

Not applicable.

REFERENCE TO SEQUENCE LISTING, A TABLE, OR A COMPUTER PROGRAM LISTING, COMPACT DISC APPENDIX

Not applicable.

TECHNICAL FIELD OF THE INVENTION

The field of the invention is methods and systems for magnetic resonance imaging (MRI) applied particularly to whole-body, brain and other body part magnetic resonance (MR) imaging as well as to sample MR characterization. More specifically, the invention may be related to methods and systems for correcting motion-induced phase errors, particularly in high-productivity MRI, in Diffusion- and/or Perfusion-Weighted Magnetic Resonance Imaging (further generalized as DW-MRI), including Diffusion and/or Perfusion Tensor MRI (DT-MRI).

BACKGROUND OF THE INVENTION

When a sample or a human body or its part (further generally mentioned as "a sample") is subjected to uniform polarizing magnetic field (usually high-strength stationary magnetic field $B_0$=1 . . . 3 T, up to 7T, used for medical imaging, or low-strength—$B_0$=0.05 . . . 0.5 T, used for security imaging as well as for nuclear magnetic resonance characterization of samples), the individual magnetic moments of the spins in the subject tissue attempt to align with this polarizing field creating an equilibrium magnetization $M_0$ in the tissue, which is proportional at equilibrium to the magnetic field. While the stationary magnetic field is applied along z-axis of MRI apparatus, the tissue is subjected to cyclically applied excitation field $B_1$ in the x-y-plane generated by a resonance frequency (RF) coil, particularly to at least one electromagnetic near-resonant radio-frequency pulse (RF excitation pulse applied with resonant Larmor precessing frequency, which is proportional to $B_0$, 42.58 MHz/T for hydrogen). With RF excitation pulses applied in the presence of a slice-selection gradient, the net aligned (longitudinal) magnetization $M_z$ may be tipped into the x-y-plane producing transverse magnetization $M_{xy}$ in a selected 2D slice. The longitudinal magnetization $M_z$ tends to $M_0$ with characteristic spin-grid relaxation time $T_1$. The transverse magnetization is susceptible to Landau-Lifshitz-Gilbert damping; $M_{xy}$ relaxation in the tissue is characterized by spin-spin relaxation time $T_2$. The energy content of the RF pulse determines the amount of excited spin which is capable of emitting a MR signal. The transverse magnetization is characterized by its ratio to the longitudinal magnetization, or by a flip angle $\alpha$ of a RF excitation pulse. The MR signal emitted by the excited spins after so-called echo time provides information related to the properties of the tissue; the MR signal may be acquired to characterize the sample forming data sets from its different locations and to form, in such a way, an image, which may be, for example, a $T_2$-weighted image. Typically, the region to be imaged is scanned by a sequence of varying magnetic field gradients, which are spatially encoded in all three spatial directions using gradient coils with necessary gradient waveforms applied. The resulting set of received echo signals acquired by appropriate RF reception coils in each measurement cycle is digitized and processed using one of well-known image reconstruction techniques.

A tissue layer (slice) location is selected in a spatial direction defined as a slice-selection direction (S-direction usually corresponding to z-direction) by applying in this direction a layer-selection (slice-selection) $G_x=G_S$ gradient simultaneously with the excitation RF pulse. For the purpose of achieving local resolution in a second spatial direction defined as a phase-encoding direction (P-direction usually corresponding to x-direction), typically a so-called phase-encode $G_x=G_P$ gradient is temporary imposed in this direction, which ensures dephasing after the excitation RF pulse and rephasing prior to the detection of the MR signal of oscillating spins along said direction. The phase-encoding gradient is turned on and off after each excitation RF pulse with different gradient magnitude to encode/decode the received signals in the x-direction before data is collected with the readout gradient applied. In a third spatial direction defined as a readout direction (R-direction usually corresponding to y-direction), typically a so-called frequency-encode $G_y=G_R$ gradient is imposed, usually synchronized with the phase decoding and with signal acquiring. To encode/decode signals in the y-direction, the signals are detected in the presence of so-called frequency-encode or readout gradient, to enable collecting a line of data points with different precession frequency corresponded to a single RF excitation pulse and their mapping into a spatial frequency domain known as k-space. Since phase and frequency are separately dependent upon a location along P- and R-direction correspondingly, it is possible to reconstruct a MR image in xy-plane sampling k-space signal prior to Fourier transformation.

The $T_2$-weighting sequence applied to the same slice is repeated with different phase encoding with period $T_R$, a repetition time. $T_R$ determines the spin echo sequence duration; the longer the $T_R$ (up to and over 2000 milliseconds), the more complete the longitudinal magnetization regrowth and correspondingly the greater initially excited transverse magnetization $M_{xy}$. Associated with greater $M_{xy}$ and longer echo-time $T_E$ (80 to 140 ms), the different tissues are better highlighted according to their spin-spin relaxation time $T_2$ (which should exceed $T_E$ and may be as low as 150-200 ms). However, the long repetition time results in long acquisition time.

The diffusion-weighted MR imaging (DW-MRI or DWI) is a $T_2$-weighted imaging method, which may be used for early detection of brain infarcts as well as for detection of liquid explosives and for characterization of hydrocarbon-bearing formation samples. The at least one pair of diffusion-weighting gradient pulses are applied along one axis or consequently along plural gradient axes, with time interval between beginnings of first and second gradient pulses called diffusion time interval Δ. The diffusion-weighted preparatory sequences ensure that a molecular movement which occurs in the observed voxel as a result of diffusion processes produces an identifiable attenuation of the $T_2$-weighted MR signal, according to the following equation known as a partial solution of Bloch-Torrey differential equation for transverse magnetization $M_{xy}$:

$$S = S_0 \exp(-bD), \qquad \text{Eq. (1)}$$

where, S, $S_0$ are signal intensities with and without applying diffusion gradients; D is apparent diffusion coefficient (ADC); b is a variable dependent upon parameters of the respective preparatory sequence and the gyro-magnetic ratio for protons $\gamma = 2.67 \cdot 10^8$ rad/(s·T); in the most common case of one pair of diffusion-weighting gradient pulses of magnitude G and duration δ, it's determined by the formula:

$$b = (\delta \gamma G)^2 (\Delta - \delta/3). \qquad \text{Eq. (2)}$$

In order to obtain effective diffusion-weighting, i.e. effective identifiable attenuation determined by diffusion, and to determine ADC with acceptable accuracy, generally b-value in the range of 500-2000 s/mm² is required; diffusion times in the state-of-the-art techniques at restricted gradient values are usually of order 20-40 ms. Such diffusion time order corresponds to diffusion path (Einstein's mean radial displacement) $\langle z \rangle = (\delta D \Delta)^{1/2}$ of order 10 μm, which determines boundary restrictions (blur).

The standard diffusion-weighting method has its origins in the Stejskal-Tanner experiment (see: "Spin-diffusion measurements: spin echoes in the presence of a time-dependent field gradient" by E. O. Stejskal, J. E. Tanner, *J. Chem. Phys.*, Vol. 42, 1965, p. 288-292). The spin-echo sequence comprises a 90° excitation and 180° refocusing RF pulses and at least one pair of diffusion-weighting gradient pulses. As a method of refocusing the MR signal for its detection, the so-called spin echo-signal is produced by refocusing the RF magnetic field by means of an additional refocusing RF pulse, commonly with flip-angle 180° (or, for example, two 90° RF refocusing pulses in a case of so-called stimulated echoes), which is excited in the presence of the same slice-selection gradient, particularly, in a half spin-echo time $T_E/2$ after the initial excitation RF pulse, where another half spin-echo2 time $T_E/2$ is a time between the refocusing RF pulse and MR signal detection. Spin-echo sequence is well combined with Echo-Planar Imaging (SE-EPI) method of image acquisition comprising acquiring multiple k-space lines in a single shot (rapid sequence of echoes with alternation of the polarity of the read gradient during 20-80 ms) that avoids decreasing SNR (signal-to-noise ratio). The signal intensity S is determined at DWI for every voxel accordingly to Eqs.(1), (2) by choice of gradients and diffusion times within echo time $T_E$ during which the peak signal is obtained. For the sample characterization, the scan results may be compared at different diffusion-weighting characteristics. For obtaining comparable results of different DWI experiments, the motion compensation is desirable.

However, for modern high-resolution diffusion sequences with standard SE-EPI protocol characterized by long readouts, total acquisition time approaches to 14-20 min and more, which is clinically unacceptable; the higher image resolution comes at a cost of sufficiently increased scan time and the blur associated with $T_2^*$ spin-spin decay. The image spatial resolution is low, as the number of consecutively detectable echoes at given echo time $T_E$ is very limited by the naturally short effective spin-spin relaxation time $T_2^*$, which relaxation includes irreversible decay caused by static field magnetic susceptibility inhomogeneities. From the other hand, the gradient values are limited by the gradient coil performance limits and the safety issues; at that achieving sufficient b-value requires increasing Δ and $T_E$. At larger Δ, the image becomes more sensitive to the higher-order derivatives of the body bulk motion; therefore, the motion compensation is desirable, especially at steep diffusion gradients.

In the alternative gradient-echo sequence without the refocusing RF pulse, the pair of gradient pulses has a form of two lobes with opposite polarity (bipolar gradient—BG pulses). The polarity inversion of the magnetic field gradient is used for refocusing after dephasing created by the first polarity part of the BG pulse. Due to large phase shifts from small patient bulk translations, the gradient-echo DWI is exquisitely sensitive to motion because of absence of polarity and phase velocity reversing by the 180° refocusing RF pulse. For example, at BG diffusion-weighting pulse characteristics G=40 mT/m, δ=20 ms, Δ=30 ms, value b=580 s/mm² is achieved. At that, in the event of macroscopic movement x of the human body, π-order phase shift in the MR signal is occurred at the local velocity of order 0.3 mm/s, which shift is generally determined by the formula:

$$\phi \sim \gamma G \delta. \qquad \text{Eq. (3)}$$

As no 180° rephasing pulse is used, the relaxation due to fixed causes is not reversed; the loss of signal resulting from low effective spin-spin relaxation time $T_2^*$ result in lower signal-to-noise ratio SNR. For decreasing boundary blur and motion artifact effect, the diffusion time interval Δ may be limited, then obtaining quality images may be complicated. Ultimately, the motion compensation should be used.

An example of the steady-state gradient-echo refocusing method is given by the Diffusion-Weighted Steady-State Free Precession (DW-SSFP) imaging method (see: "Steady-state diffusion-weighted imaging: theory, acquisition and analysis" by J. A. McNab and K. L. Miller, *NMR Biomed.*, Vol. 23, 2010, p. 781-793). Steady-state imaging involves the repeated application of identical sequences of low angle RF excitation pulses and a DWI gradient waveforms synchronized accordingly to net magnetization rotation; at that each sequence is unbalanced with respect to the first derivative of bulk motion. At lower flip angle α, the recovery of the residual longitudinal magnetization for a given $T_1$ will be sufficiently complete at shorter $T_R$; at that shorter echo time $T_E$ is required to provide sufficient signal strength at acquisition.

The longitudinal magnetization gradient created by DWI gradient waveform coupled with low-angle RF excitation (usually α=15-30°) determines the drift-diffusion effect multiplying the magnetization mobility (diffusivity) in the longitudinal direction, which can be easily detected as a greater attenuation of $T_2^*$-weighted signal. (Strictly speaking, the quasi-steady-state free precession with cyclical drift of the spins takes place in a case of DW-SSFP with longitudinal diffusion gradients; however, consistently with established terminology, below it's referred as a steady state with cyclical drift or free precession with cyclical drift). While the complicated interdependence of the diffusion terms and the nondiffusion terms (especially in the case of unbalanced gradients) make it difficult to build intuition for how DW-SSFP pulse sequence will behave for a given parameter choice and/or tissue type and to find required diffusion-weighting parameters, experiments show an apparent diffusion coefficient anisotropy at steady state—increasing ADC in z-direction as high as up to 2-10 times, which may be explained by drift-diffusion effect in the presence of the magnetic field gradient co-directed with polarizing magnetic field and longitudinal magnetization.

However, DW-SSFP is practically very difficult to apply to in vivo imaging due to strong sensitivity to motion at repeated excitation technique. Because steady-state sequences conserve residual transverse magnetization, these sequences are extremely sensitive to motion artifacts arising due to a phase shift caused by translation in the diffusion gradient direction and to a phase gradient caused by the tissue deformation in the diffusion gradient direction, or by rotation in the plane perpendicular to the diffusion gradient direction.

Multi-slice MRI imaging is known from the prior art. In the method of multi-slice SSFP facilitating multi-slice coherent imaging according to U.S. Pat. No. 7,514,927 to Herzka and Winkelmann, issued 2009 Apr. 7, for a plurality of mutually perpendicular steady spin-state slices, time-domain multiplexed readouts are performed with applying phase-encode gradients in the mutually perpendicular directions; acquired magnetic resonance data in each readout correspond to one of the steady spin-state slices. Radio frequency excitation pulses are interleaved with the time domain multiplexed readout pulses to maintain the steady spin-states of the slices. The acquired magnetic resonance data are reconstructed to produce reconstructed images corresponding to the plurality of slices. In such a way, the multi-slice coherent imaging reduces general acquisition time.

However, the mutually-perpendicular multi-slice imaging is related to the noise amplification; it's extremely sensitive to motion artifacts, especially at diffusion-weighting; its applicability for DW-SSFP is strictly limited.

In the method for simultaneous multi-slice MRI according to U.S. patent application Ser. No. 12/761,314 to Setsompop and Wald, published 2011 Oct. 20 (2011/0254548 A1), image data is acquired simultaneously from multiple slice locations using a RF coil array. Following RF excitation, at least one readout gradient is applied along frequency-encode direction in order to form echo-signals. For separating of aliased pixels at multi-slice acquisition, a modified SE-EPI sequence includes a series of slice-encode gradient "blips" contemporaneously with phase-encoding blips in the presence of alternating readout gradients common to EPI sequences. The slice-encoding blips are designed to impart a phase shift accruals to the formed echo-signals; the image data corresponding to each sequentially adjacent slice location is cumulatively shifted by a fraction of the imaging FOV in the phase-encoding direction (field-of-view, which for a conventional brain image may be equal to ~24 cm). This fraction FOV shift in the image domain provides separation of the aliased signal data with substantial suppression of pixel tilt and blurring at the image reconstruction. For diffusion-weighting in a selected direction, two diffusion gradients are applied prior to applying the at least one readout gradient.

However, this method based on a phase shift by a fraction of FOV is very sensitive to a phase shift due to the second derivative of patient bulk motion; the motion compensation is required for avoiding motion artifacts.

A useful gradient echo may be generated using Fast Low-Angle Shot (FLASH) sequence comprising crusher gradient pulse for eliminating in each cycle residual transverse magnetization, which, however, entails the high noise level. The higher SNR and CNR are provided by the Fast Imaging with Steady Precision (True-FISP) technique that uses fully balanced gradient waveform. The elements of both techniques are used in method of reducing imaging scan times according to U.S. Pat. No. 8,076,936 to Borthakur e.a., issued 2011 Dec. 13, the sequence comprises a $T_{1\rho}$ preparation period including applying a first non-selective $90_x°$ magnetization-flipping RF pulse, one or more phase-alternating spin-locking $90_y°$ RF pulses to provide $T_{1\rho}$ contrast reducing image artifacts resulting from $B_1$ inhomogeneity, a second non-selective $90_{-x}°$ RF magnetization-flipping pulse to return the magnetization to the longitudinal axis (with characteristic $T_{1\rho}$ relaxation time); followed by a balanced gradient echo sequence for image acquisition including applying at least one $\alpha/2_{-x}$ excitation pulse followed by balanced pairs of phase-alternating spin-locking $\alpha_x$ and $\alpha_{-x}$ pulses and magnetization-spoiling crusher gradient pulse to reduce blurring caused by the approach to the steady-state; followed by acquiring multiple lines of k-space and allowing magnetization to relax toward equilibrium magnetization (with possible relaxation period shortening to the time 0.3-0.4 s instead of 2-4 s and using model of magnetization saturation).

However, applying the balanced pairs of phase-alternating spin-locking impulses and additional crusher gradient pulse is associated with higher noise and significant signal loss incurred when the balance is not fully restored; the motion compensation is desirable.

In vivo intra-voxel incoherent motion MRI technique may be used, particularly, for the blood flow measurement; a perfusion tensor may be obtained. The method of perfusion imaging according to U.S. Pat. No. 7,310,548 to Van Den Brink, issued 2007 Dec. 18 comprises performing a first magnetic resonance data acquisition at a zero or very low sensitivity ($b_1=0$) value, performing a second set of at least six magnetic resonance data acquisition in different directions at low sensitivity ($b_2<50$ s/mm$^2$) values; determining the perfusion tensor based on the magnetic resonance data acquisitions. For improving contrast, the method embodiment includes performing the second and a third sets at higher sensitivity ($b_2=600$-$1200$ s/mm$^2$, $b_3=100$-$400$ s/mm$^2$); determining diffusion coefficient tensor to provide a diffusion signal component; eliminating the diffusion signal component to provide perfusion signal component. The perfusion tensor computation based on the decay measuring at different sensitivities is determined by bi-exponential MR signal decay function:

$$S/S_0 = f\exp(-bP) + (1-f)\exp(-bD), \quad \text{Eq. (4)}$$

where, P is a perfusion constant (typically P=0.05-0.08 mm$^2$/s); D—diffusion constant (typically D=0.002 mm$^2$/s); f is a fraction of fluid (flowing material, representative fraction of blood content in a voxel).

Low-sensitivity spin-echo diffusion-weighted sequence with single signal acquisition allows distinguishing perfusion characterized by higher-derivative flow patterns; at that the data of computed image maps of apparent diffusion coefficient (ADC) may be fitted to a stretched model of a tissue heterogeneity index mapping. The perfusion-imaging apparatus according to U.S. Pat. No. 7,310,548 comprises MRI data acquisition device, a display unit, and a computer system programmed to perform MRI data acquisitions with at least two different low b-values and with at least one higher b-value, and is further programmed to determine diffusion signal component of the low b-value acquisitions based on the higher b-value acquisition.

However, the blood flow rates vary in a broad diapason and can't be estimated directly based on this sequences; it's time-consuming to select the sensitivity values in a working range eliminating image flow artifacts while providing resulting signal attenuation sufficient for diffusion-weighting analysis. While useful signal not containing the flow velocity derivatives is analyzed, practically it's difficult to distinguish perfusion flow from higher-order bulk motion derivatives and to eliminate diffusion signal component. For obtaining comparable results in different diffusion-weighting experiments, the motion compensation is desirable.

The first acquisition data set with no or very low diffusion-weighting may be used as a target image, particularly, to construct a phase map in k-space; at that spatial misalignment may take place. The phases from the higher weighted data may be combined with the phase map of the first set with eliminating a motion induced phase shift and forming the adjusted data set using correlation coefficient similarity measure (see: "Correction of motional artifacts in diffusion-weighted images using a reference phase map" by A. M. Ulug et al., *Magnetic Resonance in Medicine*, Vol. 34, No. 2, 1995, pp. 476-480).

However, the motion artifacts are very difficult to avoid at the phase shifts more than $\pi(180°)$, which is determined by diffusion sensitivity accordingly to Eq. (3); said phase shift is decoded as a space parameter.

In another method of correcting spatial misalignment using normalized mutual information similarity measure, the images are registered to a normalized template using a mutual information-based registration technique and employing a spatial transformation model containing state-of-the-art dependencies to correct the eddy current-induced image distortion and rigid body motion in three dimensions (see: "Comprehensive Approach for Correction of Motion and Distortion in Diffusion-Weighted MRI" by G. K. Rohde et al., *Magnetic Resonance in Medicine*, Vol. 51, No. 1, 2004, pp. 103-114).

However, sufficient patient motion and tissue deformation may lead to the misregistration of subsequent image nodes (phase-encode lines in 2D images or slices in 3D images).

In the method of acquiring MRI image according to U.S. Pat. No. 6,842,000 to Norris and Driesel, issued 2005 Jan. 11, double spin-echo $T_2$-weighted preparatory sequence comprises a $90_x°$ RF excitation pulse followed by two pairs of bipolar diffusion gradients (BG pulses) and a $180_y°$ RF refocusing pulse between two gradients of each pair, at that each of the $90_x°$ excitation pulse and the $180_y°$ refocusing pulses are applied in the presence of the layer-selection $G_z=G_S$ gradient. The double spin-echo occurs and two gradient navigator echoes are generated consecutively during the second spin echo of the preparatory sequence; the navigator echoes contain bulk motion characteristics measured as an interference variable. The disturbing phase changes are measured at points of corresponding spin echo maximums and then a navigation signal is analyzed and the phase characteristics of transversal magnetization are corrected by compensation pulses. At that a homogeneous magnetic field pulse dimensioned to compensate the zero-order phase shift and magnetic field gradient pulses dimensioned to compensate the phase gradients measured by the navigator signal interference are applied in the direction of the stationary longitudinal magnetic field and in the correspondent spatial directions. In a case the direction of the diffusion gradients is the same as S-direction, P- and R-components of the phase gradient are encoded separately in the navigator echoes; the corrective gradient pulses are applied in the P- and R-direction respectively. Because spatial encoding-decoding is not done during $T_2$-weighted preparatory imaging sequence, a $90_{-x}°$ driven equilibrium Fourier transform pulse is applied at the time of the last spin-echo rotating the transversal magnetization back onto the longitudinal axis, its phase may be shifted to compensate the measured motion-related phase shift. It may be followed by an image acquiring sequence with N consecutive periodic cycles with phase encoding-decoding P- and R-gradient pulses changed from cycle to cycle to fill the various lines of the k-space used to reconstruct the image, for example, the FLASH sequence of partial experiments with a short repetition time $T_R \ll T_1$ in each time containing an excitation with the flip angle $\alpha<90°$.

Apparatus for the MRI data acquisition according to U.S. Pat. No. 6,842,000 comprises a magnet for generating constant $B_0$ field, an additional coil for generating parallel homogeneous magnetic field $B_z$, gradient coil sets for generating gradients $G_x$, $G_y$, $G_z$, a power supply unit comprising a RF generator and gradient coil power supplies, a RF coil and a selection unit for selecting the MRI signals, a control unit comprising a correction control path. The control unit controls selection of MRI signals and uses the interference variables of the navigation signal for the correction of bulk motion artifacts by changing the characteristics of the transversal magnetization; the correction control path configuration allows upon activation thereof to apply a homogeneous magnetic pulse in the direction of the stationary magnetic field dimensioned to compensate for the phase shift and to apply magnetic gradient pulses to compensate the phase gradient for the transversal magnetization.

In the navigator echo technique, displacement of the moving subject is measured for each location by the shift of the image space navigator echo compared to a reference echo. However, it's difficult to correctly assign phase shift to the correspondent location because the motion-disturbed phase characteristics of the navigator echoes are incompatible by phase in k-space. The data acquisition by followed FLASH sequence is more time-consuming than widely used SE-EPI method; at that the image spatial resolution is impaired.

Summarizing, using the known high-productivity MRI techniques, such as SE-EPI, may lead to motion-related phase misregistration and artifacts. Particularly, the known diffusion-weighting MRI methods achieve required quality at the cost of high diffusion-weighting gradient sensitivity, long diffusion and repetition time, generally resulting, for gradient-echo sequences, in high sensitivity to bulk motion and vibration and, for spin-echo sequences, to higher-order motion derivatives. The known methods of motion compensation don't sufficiently achieve the goals of artifact elimination at sufficient bulk motion, of distinguishing bulk motion from perfusion, etc.

SUMMARY OF THE INVENTION

To sufficiently decrease sensitivity to a bulk motion of a subject (such as a human body or its part, or a sample) at high-productivity MRI and/or at diffusion-weighting MRI (DW-MRI), such as whole-body MRI, detecting drift-diffusion at DW-MRI, distinguishing flow and perfusion in the imaging location from the bulk body motion, the method for magnetic resonance imaging is proposed, which is based on transverse magnetization excitation in an additional (reference) slice location and a motion compensation based on a determined reference echo signal phase shift.

In a method for magnetic resonance imaging, an imaging volume is subjected to at least one sequence of resonance frequency (RF) pulses and gradient magnetic field pulses (gradients), each RF pulse of the at least one sequence is applied in a presence of a gradient. The method comprises, in the at least one sequence:

applying at least one first excitation RF pulse within at least one first excitation resonance-frequency range in order to excite transverse magnetization within at least one first slice location within the imaging volume and to form at least one first echo signal from the first slice location;

applying at least one second excitation RF pulse within at least one second excitation resonance-frequency range in order to excite transverse magnetization within at least one second slice location within the imaging volume, the at least one second slice location is distinguished from the at least one first slice location, and to form, prior to the at least one first echo signal, at least one second echo signal from the at least one second slice location; and acquiring the at least one first and the at least one second echo signals in order to form a corrected data set, wherein, of the at least one first and the at least one second echo signals, at least one echo signal is formed with phase encoding, at least another echo signal is at least one reference echo signal, at least one phase shift of the at least one reference echo signal is at least one reference phase shift, a motion-related phase shift of the at least one echo signal is compensated based on the at least one reference phase shift.

In the preferred embodiment of the method, the at least one first excitation RF pulse is applied in a presence of at least one first gradient; the at least one second excitation RF pulse is applied, after the at least one first excitation RF pulse, in a presence of at least one second gradient; the at least one reference echo signal is formed without phase encoding.

In the preferred embodiment of the method, the at least one second gradient is at least one diffusion-weighting gradient applied along at least one diffusion-weighting direction; the at least one second excitation RF pulse is at least one reference excitation RF pulse, which is applied within at least one reference excitation resonance-frequency range in a presence of the at least one diffusion-weighting gradient; the acquiring of the at least one second echo signal is performed in a presence of the at least one diffusion-weighting gradient in order to determine the reference phase shift; the acquiring of the at least one first echo signal is performed in a presence of at least one readout gradient in order to phase encode a location within the first slice location.

In the method preferred embodiment, at least one balancing RF pulse is additionally applied in a presence of the at least one diffusion-weighting gradient in order to balance transverse magnetization within the at least one second slice location after the acquiring of the at least one reference echo signal and prior to the acquiring of the at least one first echo signal.

In the method preferred embodiment, the at least one reference excitation RF pulse is applied within at least two reference excitation resonance-frequency ranges; the at least one reference echo signal from at least one second slice location is at least two reference echo signals from at least two second slice locations; the at least one reference phase shift is at least two reference phase shifts; a gradient of the at least two reference phase shifts with respect to the at least one diffusion-weighting direction is determined in order to characterize deformation along the at least one diffusion-weighting direction.

In the preferred embodiment, at least one compensation sufficiently uniform magnetic field pulse dimensioned to compensate the at least one motion-related phase shift and/or at least one compensation gradient magnetic field pulse dimensioned to compensate the gradient of the at least two phase shifts with respect to the at least one diffusion-weighting gradient direction are applied prior to the acquiring of the at least one first echo signal.

In the method preferred embodiment (symmetrical sequence), the at least one diffusion-weighting gradient comprises at least one pair of diffusion-weighting gradients having same polarity; a refocusing RF pulse is applied about symmetrically between diffusion-weighting gradients of the at least one pair in order to form a symmetrical sequence, which is characterized by a first derivative of the at least one reference phase shift being about compensated, in order to characterize transverse magnetization diffusion in the at least one first slice location.

In another preferred embodiment (asymmetrical sequence), the at least one diffusion-weighting gradient comprises at least one pair of diffusion-weighting gradients having same polarity; a refocusing RF pulse is applied with asymmetrical shift between diffusion-weighting gradients of the at least one pair in order to form an asymmetrical sequence, which is characterized by a first derivative of the at least one reference phase shift being uncompensated, in order to characterize flow and/or perfusion in the at least one first slice location.

In another preferred embodiment (asymmetrical sequence), the at least one diffusion-weighting gradient comprises at least one pair of diffusion-weighting gradients having opposite polarities in order to form an asymmetrical sequence, which is characterized by a first derivative of the at least one reference phase shift being uncompensated, in order to characterize flow and/or perfusion in the at least one first slice location.

In the preferred embodiment of the method (free precession method with reversible magnetization drift), the at least one first excitation RF pulse and the at least one reference excitation RF pulse are applied with a partial flipping angle 15-60°, preferably 20-30°; the at least one reference excitation RF pulse is applied with a flipping angle at most equal to the flipping angle of the at least one first excitation RF pulse; the at least one diffusion-weighting gradient is a unipolar diffusion-weighting gradient; the at least one diffusion-weighting direction is about the magnetic field direction in order to form an asymmetrical diffusion-weighted sequence, which is characterized by a first derivative of the at least one reference phase shift being uncompensated, in order to characterize a transverse magnetization drift along the magnetic field direction in the at least one first slice location.

In a method for magnetic resonance imaging, an imaging volume is subjected to at least one first and at least one second diffusion-weighted sequences of resonance frequency (RF) pulses and gradient magnetic field pulses (gradients), in order to form, correspondingly, a first and a second corrected data sets, the method comprising, in each of the at least one first and the at least one second diffusion-weighted sequences, applying at least one first excitation RF pulse within at least one first excitation resonance-frequency range in a presence of a slice-selection gradient in order to excite transverse magnetization within at least one first slice location within the imaging volume and to form at least one first echo signal from the at least one first slice location;

applying, after the at least one first excitation RF pulse, at least one reference excitation RF pulse within at least one second excitation resonance-frequency range in a presence of at least one diffusion-weighted gradient in order to excite transverse magnetization within at least one second slice location within the imaging volume and to form, prior to the at least one first echo signal, at least one reference echo signal from the at least one second slice location; and acquiring the at least one first echo signal with phase encoding and the at least one reference echo signal without phase encoding, at least one phase shift of the at least one reference echo signal is at least one reference phase shift, the at least one reference phase shift is determined in order to compensate a motion-related phase shift of the at least one first echo signal, wherein, the second diffusion-weighted sequence is asymmetrical, i.e. characterized by a first derivative of the at least one reference phase shift being uncompensated, the at least one reference phase shift of the at least one first diffusion-weighted sequence is being sufficiently distinguished from the at least one reference phase shift of the at least one second diffusion-weighted sequence in order to distinguish a flow and/or perfusion component from a diffusion component of transverse magnetization decay in the first slice location based on a comparison of the first and the second corrected data sets.

In the preferred embodiment of the DW-MRI method, the first diffusion-weighted sequence and the second diffusion-weighted sequence are both asymmetrical and characterized by the reference phase shifts of said first and second sequences being mutually opposite.

In the preferred embodiment of the method, the first diffusion-weighted sequence is about symmetrical, i.e. characterized by a first derivative of at least one reference phase shift being about compensated, in order to characterize the diffusion component of the transverse magnetization decay in the first slice location; the second diffusion-weighted sequence comprises at least six asymmetrical sequences having different diffusion-weighting directions in order to characterize a perfusion tensor in the first slice location after eliminating the diffusion component.

In the preferred embodiment of the method, in each of the first and the second diffusion-weighted sequences, the at least one first excitation RF pulse is applied with a partial flipping angle being at most 60°, the diffusion-weighting gradient is unipolar, wherein, the unipolar diffusion-weighting gradient of the first diffusion-weighted sequence is applied about transversely to the magnetic field; the unipolar diffusion-weighting gradient of the second diffusion-weighted sequence is applied about along the magnetic field direction to distinguish drift component of transverse magnetization decay in the first slice location, particularly, in order to characterize a fraction of fluid.

An apparatus for magnetic resonance imaging comprises:

a resonance frequency (RF) coil means and a gradient magnetic coil means in order to subject an imaging volume to at least one sequence of RF pulses and gradient magnetic field pulses (gradients), each RF pulse of the at least one sequence is applied in a presence of a gradient;

a RF coil control means and a magnetic coil control means in order to apply at least one first excitation RF pulse within at least one first excitation resonance-frequency range, for exciting transverse magnetization within the at least one first slice location within the imaging volume and forming at least one first echo signal from the at least one first slice location within the imaging volume, and in order to apply at least one second excitation RF pulse within at least one second excitation resonance-frequency range, for exciting transverse magnetization within the at least one second slice location and forming, prior to the at least one first echo signal, at least one second echo signal from the at least one second slice location;

a receiver means in order to acquire the at least one first and the at least one second echo signals in order to form a corrected data set, the receiver means is adjusted to acquire, of the at least one first and the at least one second echo signals, at least one echo signal with phase encoding, wherein, at least another echo signal is at least one reference echo signal, at least one phase shift of the at least one reference echo signal is at least one reference phase shift; and a processor means in order to compensate a motion-related phase shift of the at least one echo signal based on the at least one reference phase shift.

In the preferred embodiment of the apparatus, the RF coil control means is additionally adjusted to apply the at least one first excitation RF pulse in a presence of at least one first gradient and to apply, after the at least one first excitation RF pulse, the at least one second excitation RF pulse in a presence of at least one second gradient; the receiver means is additionally adjusted to acquire the at least one reference echo signal without phase encoding.

In another preferred embodiment, the magnetic coil control means is additionally adjusted to apply the at least one second gradient, which is at least one diffusion-weighting gradient, along at least one diffusion-weighting direction; the RF coil control means is additionally adjusted to apply at least one reference excitation RF pulse, which is the at least one second excitation RF pulse, within at least one reference excitation resonance-frequency range in a presence of the at least one diffusion-weighting gradient; the receiver means is additionally adjusted to acquire the at least one second echo signal in a presence of the at least one diffusion-weighting gradient in order to determine the reference phase shift and to acquire the at least one first echo signal in a presence of at least one readout gradient in order to phase encode a location within the first slice location.

In the preferred embodiment, the RF coil control means is additionally adjusted to apply at least one balancing RF pulse in a presence of the at least one diffusion-weighting gradient in order to balance transverse magnetization within the at least one second slice location after the acquiring of the at least one reference echo signal and prior to the acquiring of the at least one first echo signal.

In the preferred embodiment, the RF coil control means is additionally adjusted to apply the at least one reference excitation RF pulse within at least two reference excitation resonance-frequency ranges, the at least one reference echo signal from at least one second slice location is at least two reference echo signals from at least two second slice locations, the at least one reference phase shift is at least two reference phase shifts; and the processor means is additionally programmed to determine a gradient of the at least two reference phase shifts with respect to the at least one diffusion-weighting direction in order to characterize deformation along the at least one diffusion-weighting direction.

In the preferred embodiment, the MRI apparatus additionally comprises additionally comprising the uniform magnetic coil means in order to apply, prior to the acquiring of the at least one first echo signal, at least one compensation sufficiently uniform magnetic field pulse dimensioned to compensate the at least one reference phase shift; and/or the magnetic coil control means is additionally adjusted to apply, prior to the acquiring of the at least one first echo signal, at least one compensation gradient magnetic field pulse dimensioned to compensate the gradient of the at least one phase shift (of the at least two phase shifts) with respect to the at least one diffusion-weighting gradient direction.

In contradistinction to the prior art methods, the present invention may use a phase shift of the non-phase encoded reference echo-signal accumulated due to applying the diffusion-weighting gradients in order to characterize bulk motion and tissue deformation and to compensate their effect for adjusting the magnetic resonance image. Based on comparison of symmetrical sequences (balanced with respect to first motion derivative) with different diffusion-weighting sensitivity (diffusion-weighting gradient magnitude), MR signal attenuation due to diffusion may be calculated in a case of sufficient diffusion-weighting sensitivity of at least one sequence. In a case of diffusion-weighted sequences with sufficiently reduced diffusion-weighting sensitivity, the asymmetrical sequences (unbalanced with respect to first motion derivative) may be used for distinguishing the perfusion component and thin sample structure. Particularly, the phase shift compensation may allow using the steady-state sequences with cyclical drift creating the drift-diffusion effect for decreasing scan time and/or for characterizing the fluid fraction. In a case of diffusion-weighting sensitivity being sufficient for slice-selection but may be insufficient for diffusion-weighting measurement, the symmetrical and asymmetrical sequences may be used for high-productivity MR imaging, such as using modified SE-EPI sequences with multi-slice acquisition (in this case, "diffusion-weighting" is mere a common name for the gradients applied in the specific manner than an indication of the purpose of the applying).

In contradistinction to the prior art apparatus, the present invention may combine the RF coil means providing additional (reference) excitation resonance-frequency ranges for forming the reference echo signals and the processor means programmed to adjust the magnetic resonance image representation based on a phase shift of the reference echo signals.

BRIEF DESCRIPTION OF THE DRAWINGS

There are shown in the drawings embodiments of the invention as presently preferred. However, the invention is not limited to the shown exemplary arrangements. The preferred embodiments of the invention are illustrated by schematic drawings, block diagrams, and time diagrams showing the sequence of RF and gradient pulses as follows.

It's intended that the time diagrams are given schematically over a common time axis, drawn not to scale, with following conventions. The elements of the reference phase shift balancing and the phase shift compensation are shown. Applying the compensation sufficiently uniform pulses ($C_0$) may be indicated in brackets with relation to the time scale. The slice-selection gradients are shown in longitudinal direction $G_z$; the phase-encoding gradients and readout gradients are shown in transverse directions $G_x$, $G_y$ (phase-, frequency-encode gradient directions), according to the state of the art and common definitions. The periods of forming the reference echo signal "##" and the first echo signal "$$" (cases of spin and gradient echoes) are shown with relation to the time scale.

DETAILED DESCRIPTION OF EMBODIMENTS OF THE INVENTION

The advantages of the present invention may be more readily understood with reference to the following detailed description of the embodiments taken in conjunction with the accompanying drawings.

Figure 1:
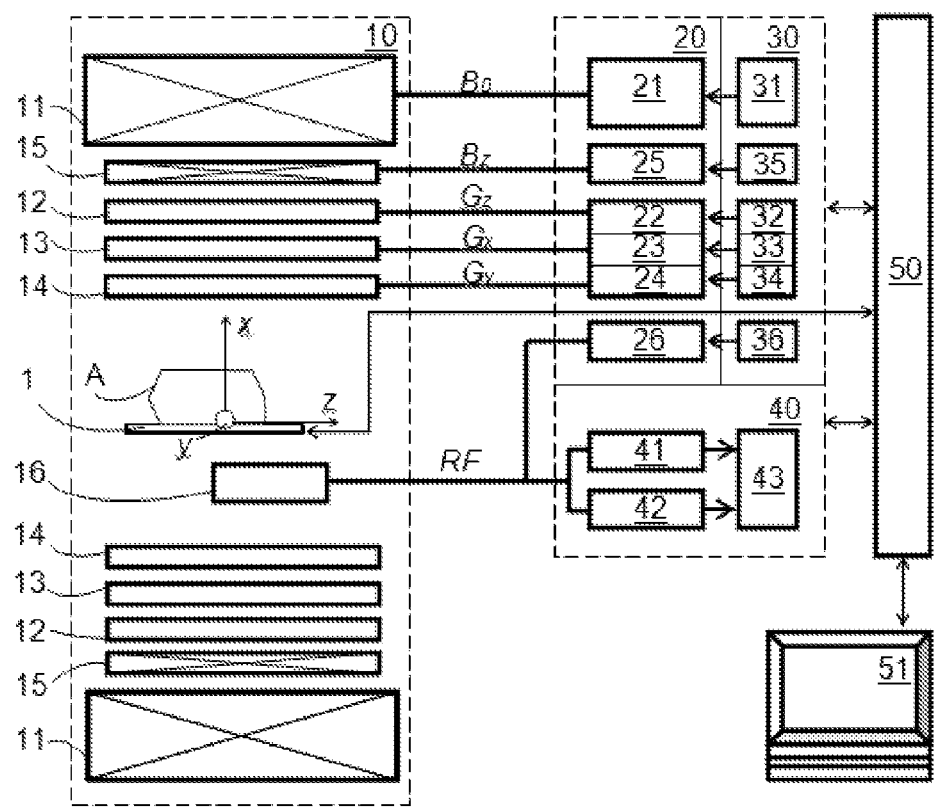
FIG. 1: A diagrammatic illustration of a MRI device comprising the apparatus for performing DW-MRI method according to invention, shown schematically and in a block form.

The DW-MRI method in accordance with the invention can be performed using a DW-MRI device as shown in FIG. 1. The DW-MRI device comprises a positioning system 1, a magnetic assembly unit 10, a power supply unit 20, system controls 30, a receiver unit (receiver) 40, a processor unit (computer) 50 having a periphery device 51. A subject (particularly patient) A is placed on a moving table of the patient positioning system 1 of the DW-MRI device, which is controlled by the computer 50.

The magnetic assembly unit 10 comprises a uniform magnetic coil means (a main magnetic coil set) 11 and controlled magnetic coil sets 12-15. The main magnetic coil set 11 is for generating a homogeneous longitudinal polarizing magnetic field $B_0$ within an imaging volume within the subject A. Gradient magnetic coil sets 12, 13, 14 are used for applying first (slice-selection) gradient pulses, second (diffusion-weighting) gradient pulses, compensation gradient pulses and readout gradient pulses. The diffusion-weighting gradients are being applied in the consequent sequences along the three diffusion-weighting gradient directions: transversal $G_x$, $G_y$, and longitudinal $G_z$. An additional magnetic coil set 15 is for generating an additional uniform magnetic field for applying compensation sufficiently uniform pulses in the longitudinal direction $B_z$. The additional magnetic coil set 15 may be integrated into the main magnetic coil set 11, or, in another embodiment, the main magnetic coil set 11 may be adjusted for applying compensation sufficiently uniform pulses $B_z$.

A RF coil set 16 (resonance frequency or radio frequency coil set) for applying excitation RF pulses for exciting transverse magnetization generally comprises a plurality of RF coils. To the RF coil set 16, exciting and refocusing RF pulses are transmitted with their frequency within a first excitation resonance-frequency range for a first slice location of the imaging volume. The RF coil set (or an array of coils) 16 is additionally adjusted for applying the additional (reference) excitation RF pulses and additional refocusing and balancing RF pulses within at least one second resonance frequency range, which is additional (reference) resonance-frequency range for exciting transverse magnetization within a second slice location of the imaging volume, which is additional (reference) location. The reference resonance-frequency range may be, in some instances, distinguished or, in other instances—at different magnitudes of the first and the second gradients, not distinguished from the at least one first excitation resonance-frequency range. In a case of RF pulse applying in a presence of the diffusion-weighted gradient, the at least one additional (reference) resonance-frequency range is determined outside the excitation resonance-frequency range and/or the echo-signal acquisition bandwidth, both adjusted to the diffusion-weighting gradient magnitude. Additional excitation and balancing RF pulses are transmitted simultaneously with the diffusion-weighting gradient pulses. Preferably, the RF coil set 16 is adjusted also for receiving MR signals irradiated from the first slice location in the imaging volume and for additional detecting of reference MR signals simultaneously with applying the diffusion-weighting gradient pulses.

The power supply unit 20, which is connected to the magnetic assembly unit 10, contains a main power supply means 21 for the main magnetic coil set 11, a power supply means (gradient amplifiers) 22, 23, 24 for the gradient magnetic coil sets 12, 13, 14, a power supply means (an additional uniform signal amplifier) 25 for the additional magnetic coil set 15, a RF transmitter 26 (transceiver) for the RF coil set 16.

The system control unit (the magnetic coil control means) 30 is connected to the power supply unit 20 for generating magnetic and RF pulses and comprises a main magnetic coil controller 31, a gradient magnetic coil control means—gradient magnetic coil controllers 32, 33, 34, an additional magnetic coil controller 35, and a RF coil control means (RF pulse generator) 36.

The gradient magnetic coil controllers 32-34 control the duration and amplitude of the currents supplied to the respective coils of the magnetic assembly unit 10. The gradient magnetic coil controllers 32-34 control timing and sensitivity of slice-select gradients, phase-encode and frequency-encode (readout) gradients, as well as consequently diffusion-weighting gradients along the respective directions, $G_z$, $G_x$, $G_y$. The gradient magnetic coil controllers 32-34 generate also the compensation gradients along the diffusion-weighting gradient directions. The additional magnetic coil controller 35 generates also the compensation uniform pulses, $B_z$. The RF coil control means (RF pulse generator) 36 controls the duration, amplitude, frequency, phase, and envelope curve of the RF pulses. The RF coil generator 36 is adjusted for generation of excitation and refocusing RF pulses within the excitation resonance-frequency range, additional (reference) excitation RF pulses, refocusing RF pulses and additional balancing RF pulses—within the corresponding reference resonance-frequency ranges determined by the corresponding gradients.

The receiver unit (receiver) 40 for receiving MR signals from the current slice location within the imaging volume comprises selection circuits 41, 42 and an analyzer 43. The selection circuits for selection and amplifying of the received MR signals include in the described embodiment an echo-signal selection circuit 41 and a reference signal selection circuit 42 for detecting and acquiring of reference MR signals simultaneously with applying the diffusion-weighting gradients. The first echo-signal acquisition bandwidth corresponds to the first excitation resonance-frequency range; the first echo-signal is encoded in dependence upon an imaging location. The additional (reference) echo-signal bandwidth corresponds to the additional (reference) excitation resonance-frequency range. The reference echo-signal bandwidth may consist of two narrow bandwidths corresponding to signals from two additional (reference) slices at the applied diffusion-weighting gradients. The reference echo-signal may be formed in a presence of a second lobe of the diffusion-weighting gradient and, thus, the reference echo-signal is not phase-encoded by location within each respected second slice location. For excluding the noise appearance in the echo-signal acquisition bandwidth, the reference echo-signal bandwidth should be compensated by the additional balancing RF pulse applying, and/or electronically by analog or digital subtraction of the reference echo-signal. An analyzer 43 comprising analog-to-digit convertor is used for digitizing the echo signal for Fourier transformation and the reference echo signal for determining reference frequency phase shift of the additionally acquired reference MR signals.

The echo-signal selection circuit 41 and a reference signal selection circuit 42 may be integrated with the RF transmitter 26 into the RF transceiver. The analyzer 43 may be integrated into computer—a processor unit (processor means) 50. The digitized scanning values are stored in the computer memory forming the so-called k-space. The processor unit (computer) 50 incorporates an image reconstruction processor and a sequence processor, and performs all necessary computations for the sequence optimization and for parameter output. Particularly, the sequence processor contains the sequence data in a sequence memory and passes the sequence data to the control unit 30.

The image reconstruction processor obtains data from the receiver unit 40; it also determines parameters of acquired bandwidths. The image reconstruction processor is programmed for reconstructing the received magnetic resonance signals encoded in dependence upon an imaging location within the imaging volume into a diffusion-weighted image representation; the diffusion-weighted image representation is adjusted based on the reference frequency phase shift of the additionally acquired MR signals. The image reconstruction processor applies a Fourier transform or other appropriate reconstruction algorithm to the detected resonance signals and stores the image magnitude data in a digital form in a memory.

In a case of DW-MRI, the image reconstruction processor may back-project the image magnitudes dividing them by the correspondent non-diffusion-weighted magnitudes based on the Eqs.(1), (2) (adjusted to the current sequence accordingly state of the art), and in such a way produces the diffusion-weighted image representation that is stored in a volumetric image memory. As another option, the perfusion-weighted image may be reconstructed based on Eq.(4).

Then, the image reconstruction processor extracts portions of the MR image representation from the volumetric image memory and formats them as an image output to display on the periphery device 51—a human-readable display or a printing device. The updated sequence processor data are entered from the periphery device 51 and transferred to the sequence processor of the processor unit 50.

The processor unit 50 may additionally include a correction processor being connected to the gradient magnetic coil controllers 32-34, the additional magnetic coil controller 35 and the RF coil control means (RF generator) 36. Receiving the analyzer 43 data and the positioning system 1 data, the correction processor calculates, based on the Eq.(3) adjusted to the current sequence accordingly state of the art, a displacement within the imaging volume and a gradient of said displacement with respect to the at least one diffusion-weighting gradient direction based on the phase (and optionally frequency) shift in the reference diffusion-weighting frequency spectrum and on a gradient of said phase (and optionally frequency) shift of the diffusion-weighting frequency spectrum accumulated during the diffusion-weighting. In such a way, the k-space data may be adjusted digitally by the correction processor based on the phase shift at the reference echo signal acquisition without compensation pulses and, optionally, without the additional balancing RF pulse and correction pulse applying.

The gradient magnetic coil controllers 32-34, the additional magnetic coil controller 35 controlled by the correction processor of the processor unit 50 may provide applying sufficiently uniform compensation pulses and compensation gradients in the at least one diffusion-weighting gradient direction, which are dimensioned to compensate phase shift of the transverse magnetization accumulated during the diffusion-weighting and a gradient of said phase shift with respect to the at least one diffusion-weighting gradient direction based on the phase (and optionally frequency) shift of the reference resonance frequency spectrum and on a gradient of said phase (or frequency) shift along the diffusion-weighting gradient direction accumulated during the diffusion-weighting.

The RF generator 36 controlled by the correction processor of the processor unit 50 may be additionally adjusted for applying the additional balancing RF pulses synchronized with the additional (reference) echo signals from the at least one additional (reference) slice location to balance the additional (reference) excitation RF pulses with compensating the reference transverse magnetization to compensate the phase (and optionally frequency) shift of the reference diffusion-weighting frequency spectrum of the additionally acquired reference MR signals accumulated during the diffusion-weighting.

In the preferred embodiment, the RF generator 36 is additionally adjusted for applying reference excitation RF pulses within at least two additional (reference) excitation resonance-frequency ranges to excite transverse magnetization within at least two additional (reference) slice locations within the imaging volume. The processor unit 50 is additionally adjusted to calculate deformation in the diffusion-weighting direction during the diffusion-weighting based on a gradient of the phase shift of the additional (reference) echo signals with respect to the diffusion-weighting directions.

In the preferred embodiment, the flow and/or perfusion component in the imaging location is determined based on the phase shift of the diffusion-weighted echo signals after eliminating the detected phase shift of the reference diffusion-weighted echo signals. The image reconstruction processor of the processor unit 50 stores in the image memory also the previous scan data and identifies the same imaging location in different diffusion/perfusion-weighted images with state-of-the-art image recognition program. The image reconstruction processor is additionally programmed to determine a perfusion tensor in the identified imaging location based on a difference of the phase shifts of the diffusion-weighted echo signal acquisitions having different phase shift characteristics (for example, at symmetrical and at asymmetrical refocusing RF pulse applying; or, in another example, at mutually symmetrical refocusing RF pulse applying in one and another sequences) after eliminating the diffusion tensor component, which is nearly identical for both sequences.

In another embodiment, the RF coil control means (generator) 36 is additionally adjusted for applying the excitation RF with partial flipping angles. The processor unit 50 stores in the image memory also the previous scan data and identifies the same imaging location in different diffusion/perfusion-weighted images with state-of-the-art image recognition program. The image reconstruction processor of the processor unit 50 is additionally programmed to determine a fluid fraction in the identified imaging location based on a comparison of the diffusion-weighted echo signals acquired at the partial flipping angle RF excitations with the longitudinal and with ones at the transversal diffusion-weighted directions. The image reconstruction processor is additionally programmed to determine a perfusion tensor in the imaging location according to the Eq. (4) and based on the determined fluid fraction and the diffusion-weighted signal attenuation in the imaging location at each diffusion-weighting direction.

Figure 2A:
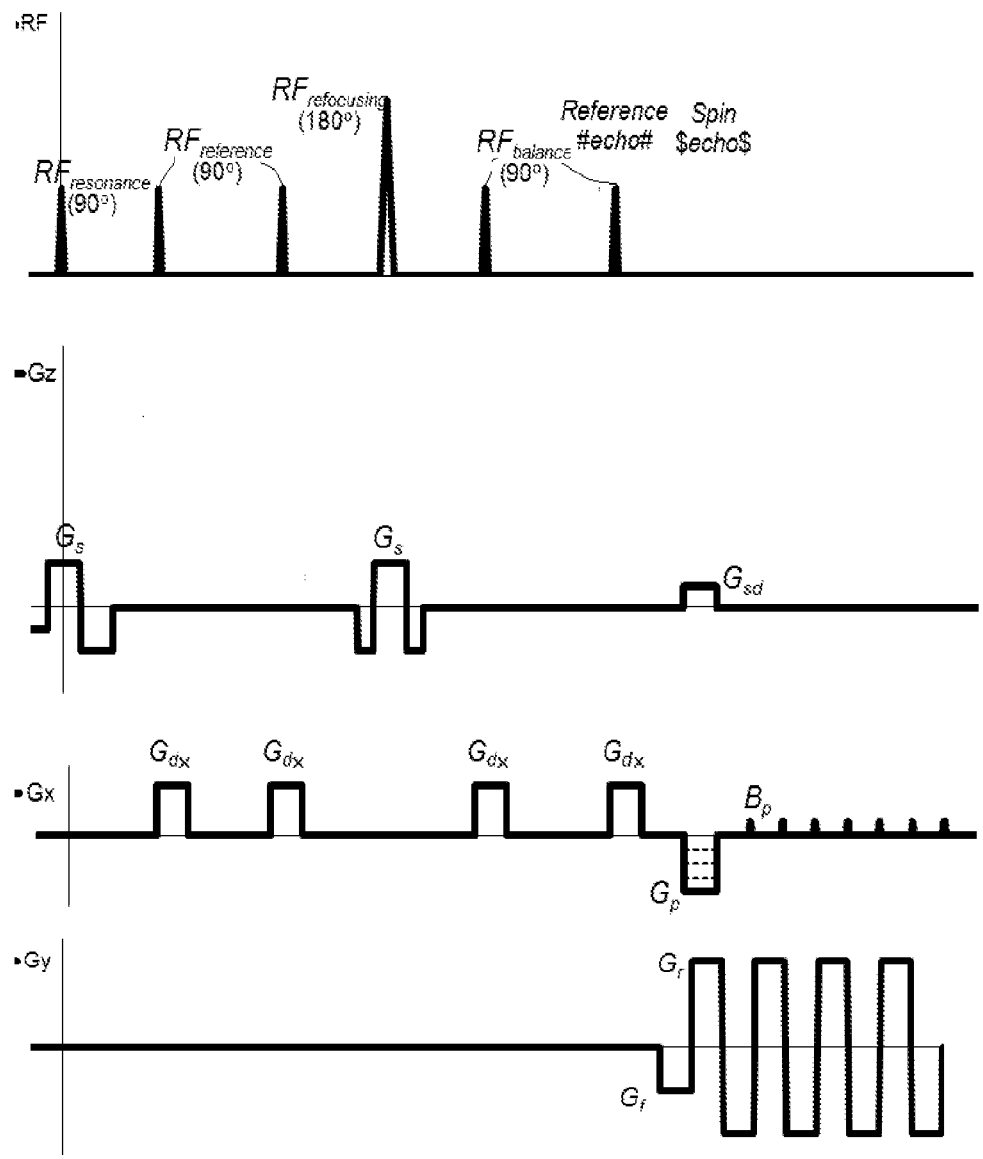
FIG. 2a: A time diagram for performing the MRI method according to the invention: a symmetrical spin-echo sequence with SE-EPI acquisition.
Figure 2B:
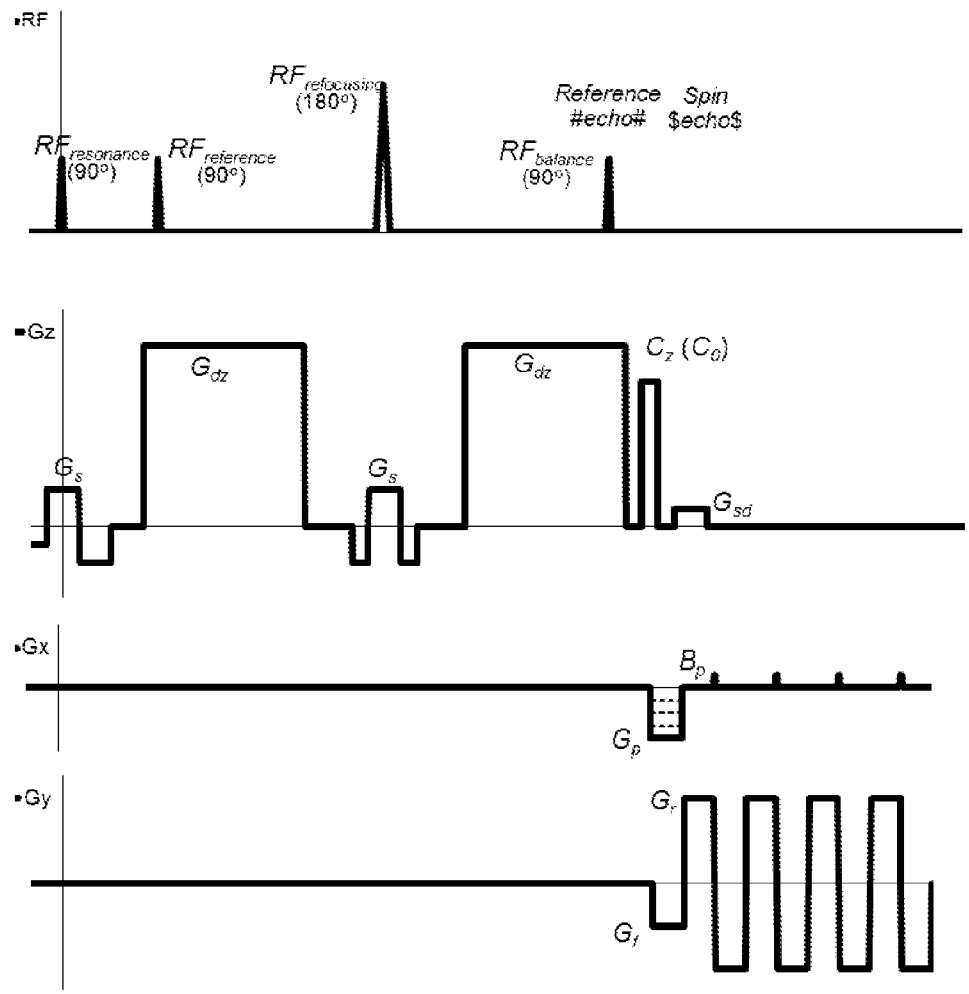
FIG. 2b: A time diagram for performing the DW-MRI method according to the invention: a symmetrical spin-echo sequence with SE-EPI acquisition.

Exemplary time diagrams for performing MRI method with a symmetrical spin-echo sequence, which is balanced with respect to the first motion derivative, are shown in FIGS. 2a, 2b. The excitation $RF_{resonance}(90°)$ and refocusing $RF_{refocusing}(180°)$ pulses are applied in a presence of the slice-selection gradients $G_s$ within a first excitation resonance-frequency range to excite transverse magnetization and to form the spin echo signal within a current (first) slice location within the imaging volume. The slice-selection gradients $G_s$ include rephasing lobes to mitigate phase dispersions introduced by the gradient. Readout gradients $G_r$ and phase-encoding gradient blips $B_p$ of the SE-EPI sequence are applied in order to acquire the spin-echo signal. The spin echo is encoded in dependence upon an imaging location within the at least one slice location as determined by applying phase- and frequency-sampling gradients $G_p$ and $G_f$ (acting around the spin echo peak) to move the first sampling point in the corresponding direction of k-space with subsequent registration phase encode lines to form 2D images for the current slice location.

In a case of high-productivity MRI with SE-EPI acquisition shown in FIG. 2a, after the excitation RF pulse and prior to the readout gradient pulses $G_r$, two diffusion-weighting gradient pairs $G_{dx}$ are applied along a phase-encode direction time-symmetrically around the refocusing $RF_{refocusing}$ (180°) pulse in order to form at least one echo signal from a current (first) slice location. Two reference excitation RF pulses) $RF_{reference}(90°)$ and corresponding balancing RF pulses $RF_{balance}$ are applied in the presence of the first and second diffusion-weighting gradients (lobes) $G_{dx}$ of each pair; each reference excitation RF pulse is applied within two additional resonance-frequency ranges in order to excite reference transverse magnetization within two additional (reference) slice locations and to form a non-phase encoded reference echo signals from each reference slice location. Second-derivative motion data may be obtained based on the reference echo signal data and extrapolated to the SE-EPI acquisition period. At least one compensation magnetic field pulse (blip), which may have gradient and uniform components dimensioned to compensate a phase shift second derivative due to the bulk translation and deformation, $B_p$ of the SE-EPI sequence, is applied after the reference spin-echo signal acquisition and prior correspondent SE-EPI echo signal acquisition from the current (first) slice location. The k-space data and a diffusion-weighted image may be also digitally adjusted after each spin-echo signal acquisition based on the bulk translation and deformation extrapolation of the reference phase shift data in order to eliminate motion-related artifacts arising during SE-EPI acquisition.

In a case of DW-MRI with diffusion weighting along z-direction shown in FIG. 2b, after the excitation RF pulse and prior to the readout gradient pulses $G_r$, diffusion-weighting gradient pair $G_d$ is applied along a diffusion-weighting direction (currently slice-encode direction z) time-symmetrically around the refocusing) $RF_{refocusing}$ (180°) pulse in order to diffusion-weight the at least one echo signal for producing a diffusion-weighted image balanced with respect to (the phase shift due to) first motion derivative. In a more special case of DT-MRI, at least six balanced consecutive sequences with different diffusion-weighting directions and at least one sequence without diffusion-weighting may be applied. Preferably, a reference excitation RF pulse $RF_{reference}$(90°) may be applied in the presence of the first diffusion-weighting gradient $G_d$ in the current diffusion-weighting direction to excite reference transverse magnetization within two additional (reference) slice locations within the imaging volume separated by 0.5-1 of the imaging volume (for example, by 14-28 slices of 28-slice volume). (In a case of diffusion-weighting in other than z directions, the additional (reference) slice locations by 0.5-1 of field-of-view FOV in the correspondent direction; the additional (reference) slices are perpendicular to the current slices in that sequence.) The reference magnetization excitation is performed within two additional reference excitation resonance-frequency ranges dependent on the diffusion-weighting gradient magnitude $G_{dz}$ forming an additional (reference) non-phase encoded echo signal (which active duration is around a balancing RF pulse $RF_{balance}$ on the RF time diagram) prior to the acquisition of the spin-echo signal. The refocusing $RF_{refocusing}$(180°) pulse, having corresponding resonance frequency ranges, flips magnetization also within two said additional (reference) slice locations. The non-phase encoded additional (reference) echo signal is acquired in the presence of the second diffusion-weighting gradient lobe of the pair in order to obtain non-phase encoded reference navigation data and to determine a reference phase shift (average over the reference slice location) of the reference transverse magnetization during the diffusion-weighting (between and during applying the lobes of the pair). The reference phase shift in a case of symmetrical diffusion-weighted sequence is determined by a second derivative of the subject bulk motion-translation and deformation (in a case of two reference slice locations) along the diffusion-weighting direction.

Data obtained due to the additional non-phase encoded reference echo signal acquisition, such as non-phase encoded reference phase shift data, may be used for correcting the image data from the current (first) slice location. In such a way, a corrected data set in k-space may be obtained.

The balancing RF pulse $RF_{balance}$(90°) may be applied to balance the reference transverse magnetization within the two additional (reference) slice locations after or around the reference echo being formed between the reference echo signal acquisition and the at least one readout gradient pulse. The additional balancing RF pulse applying and the reference diffusion-weighted echo signal acquisition are performed within the two separate additional reference excitation resonance-frequency ranges in the presence of the second diffusion-weighting gradient (second lobe) $G_{dz}$. The additional balancing RF pulse is adjusted based on the non-phase encoded reference navigation data to compensate the transverse magnetization within the two additional slice locations and its phase shifts accumulated during the diffusion-weighting.

More than one reference excitation RF pulse may be applied and more than one additional reference echo signal may be acquired in the presence of the at least one diffusion-weighting gradient pair in a case of the reference transverse magnetization phase shift exceeding ±π(180°). Additional reference excitation and balance RF pulses may be applied during the diffusion-weighting gradients $G_{dz}$ applying as well.

Motion-related data correction may be performed also by applying correction pulses. The compensation sufficiently uniform pulse $C_0$ (uniform blip) dimensioned to compensate said phase shift is applied prior to the diffusion-weighted echo signal acquisition. The dimension characteristics of the sufficiently uniform pulse (blip) $C_0$, including average amplitude and duration, are determined by a phase shift, which is a function of the product of the imaging volume first-order motion characteristics Gδx, where, G, δ are diffusion-weighting gradient magnitude and duration; x—total unbalanced displacement during the combined diffusion time interval determined between median times of dephasing and rephasing gradient lobes of the at least one diffusion-weighting gradient pair.

The gradient of the phase shift of the transverse magnetization in the two additional slice locations with respect to the current diffusion-weighting direction (the difference of averaged phase shift by each reference slice location), which is a function of a gradient of the product Gδx taking place, particularly, due to the subject deformation within the imaging volume along the at least one diffusion-weighting direction, is determined. The compensation gradient pulse (blip) $C_z$ dimensioned to compensate the gradient of said phase shift due to the subject deformation along the current diffusion-weighting direction is applied (about simultaneously with the uniform compensation pulse $C_0$) before the acquisition of the at least one diffusion-weighted echo signal.

In a case of diffusion-weighting gradient pair $G_{dx}$ applied along a current phase-encode diffusion-weighting direction x, the phase-encoding gradient blips $B_p$ of the SE-EPI sequence also may be used partially as the compensation pulses, optionally about simultaneously with uniform compensation pulses with various magnitudes. The phase- and frequency-sampling gradients $G_p$ and $G_f$ also may be applied with changing magnitudes for the deformation compensation. The k-space data and a diffusion-weighted image may be also digitally adjusted after each spin-echo signal acquisition based on the bulk translation and deformation extrapolation of the reference phase shift at a current diffusion-weighting direction. After series of measurements along six diffusion-weighting directions, the tensor of deformation may be obtained.

Figure 3A:
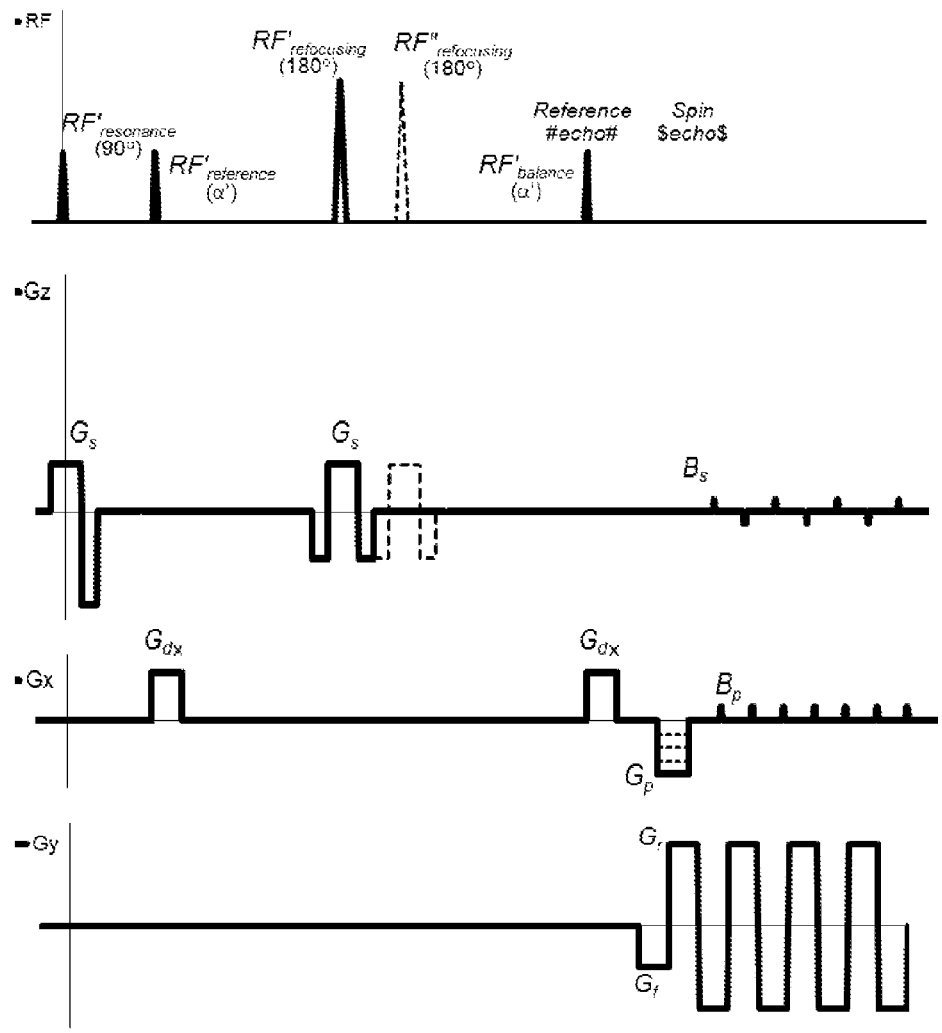
FIG. 3a: A time diagram for performing the MRI method according to the invention: an asymmetrical spin-echo sequence with multi-slice SE-EPI acquisition (the refocusing RF pulse in the sequence unbalanced with respect to the first motion derivative is shifted in time symmetrically with respect to another sequence shown by the broken line)

Exemplary time diagrams for performing multi-slice (parallel-slice) MRI method using a spin-echo sequence unbalanced with respect to the first motion derivative is shown in FIGS. 3a, b. The excitation $RF_{resonance}$(90°) and refocusing $RF'_{refocusing}$(180°) pulses are applied in two excitation resonance-frequency ranges in the presence of and dependent on the slice-selection gradients $G_s$ in order to excite transverse magnetization in two current (first) parallel slices, for example, in two aliased slice locations separated by 14 slices, and therefore the 28-slice volume is acquired over 14 shots. At that, the refocusing $RF'_{refocusing}$(180°) pulse is assymetrically shifted in order to unbalance the spin-echo sequence with respect to the first motion derivative. For bulk motion and deformation compensation, reference excitation $RF'_{reference}(\alpha')$ and balance RF pulses $RF_{balance}(\alpha')$ are applied within two reference resonance-frequency ranges in the presence of the correspondent diffusion-weighting gradient pulses in order to excite reference transverse magnetization within at least one additional (reference) slice location and to form a non-phase encoded reference echo signals from said at least one reference slice location.

In a case of high-productivity MRI with SE-EPI acquisition shown in FIG. 3a, after the excitation RF pulse and prior to the readout gradient pulses $G_r$, the diffusion-weighting gradient pair $G_{dx}$ is applied along a phase-encode direction time-symmetrically around the refocusing $RF_{refocusing}(180°)$ pulse in order to form at least two echo signals from two current (first) slice locations. A reference excitation RF pulse $RF_{reference}(90°)$ and corresponding balancing RF pulse $RF_{balance}$ are applied in the presence of the first and second diffusion-weighting gradients (lobes) $G_{dx}$, correspondingly, in order to excite reference transverse magnetization within two additional (reference) slice location and to form a non-phase encoded reference echo signals from said two reference slice location. First-derivative motion data may be obtained based on the reference echo signal data and extrapolated to the SE-EPI acquisition period. At least one compensation magnetic field pulse (blip), which may have gradient and uniform components dimensioned to compensate a phase shift due to the bulk translation and deformation, $B_p$ of the SE-EPI sequence, is applied after the reference spin-echo signal acquisition and prior correspondent SE-EPI echo signal acquisition from the current (first) slice location. The phase- and frequency-sampling gradients $G_p$ and $G_f$ also may be applied with changing magnitudes for the deformation compensation. The k-space data and a diffusion-weighted image may be also digitally adjusted after each spin-echo signal acquisition based on the bulk translation and deformation extrapolation of the reference phase shift data in order to eliminate motion-related artifacts arising during multi-slice SE-EPI acquisition. After the SE-EPI the current readout gradient $G_r$ and along with the phase-encoding gradient blips $B_p$, the alternating slice-encoding gradient blips $B_s$ may play out in order to shift the image of every other slice by one-half FOV along the phase-encode direction producing 180° phase shift between the adjacent slice locations preventing the image blurring, which could occur due to slice plurality in 3D images. As is known in the art, the foregoing pulse sequence is repeated plurality of times with a different slice-selection gradient $G_s$ being applied in each repetition such that multiple sets of a plurality of slice locations are sampled. The gradient blip $B_s$ with a compensation blip (pulse) component or the phase-encoding gradient blip $B_p$ may be applied with corrected gradient magnitude dimensioned along with uniform blip compensation pulses to compensate for deformation and for bulk motion in the corresponding directions during the single-shot SE-EPI sequence acquisition and to avoid misregistration of subsequent image nodes (phase encode lines in 2D images or slices in 3D images) associated with the blur in the obtained image.

Figure 3B:
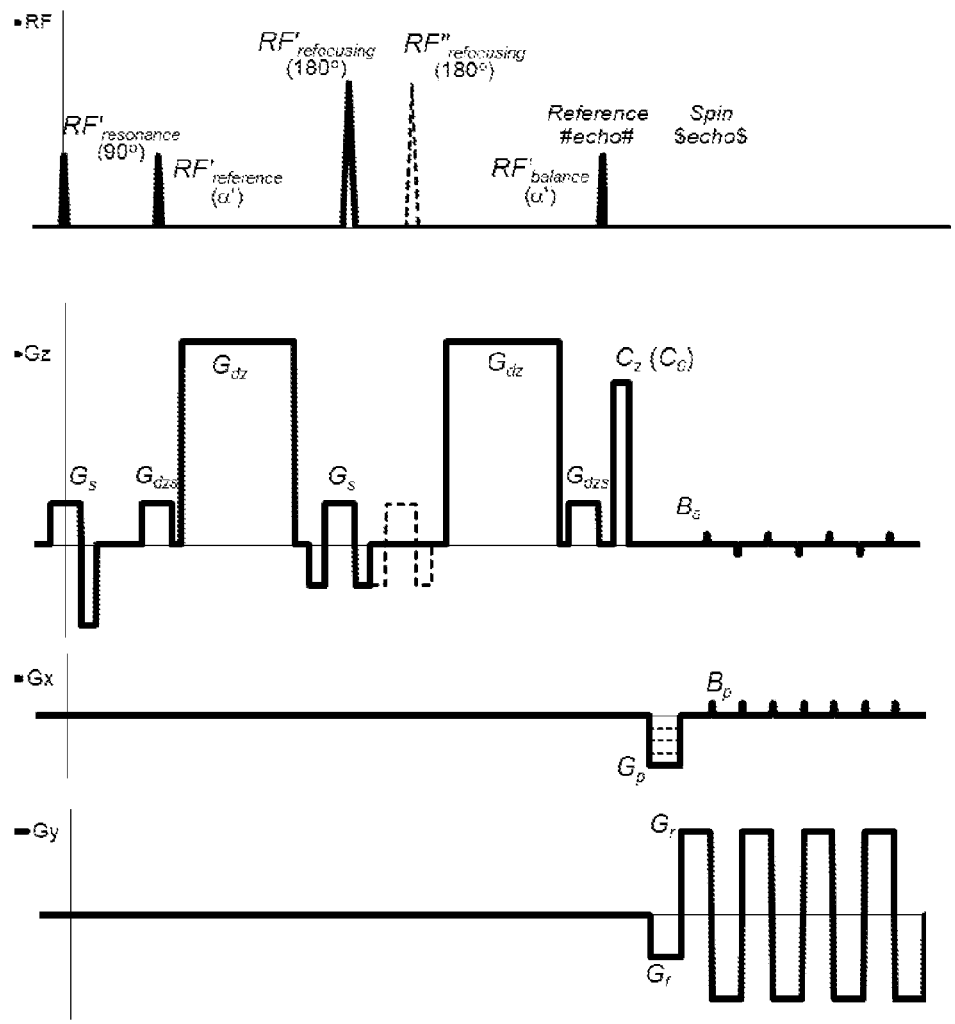
FIG. 3b: A time diagram for performing the DW-MRI method according to the invention: an asymmetrical spin-echo sequence with multi-slice SE-EPI acquisition (the refocusing RF pulse in the sequence unbalanced with respect to the first motion derivative is shifted in time symmetrically with respect to another sequence shown by the broken line)

In a case of DW-MRI with diffusion weighting along z-direction shown in FIG. 3b, reference excitation $RF'_{reference}(\alpha')$ and balance RF pulses $RF'_{balance}(\pi')$ are applied in the presence of the additional diffusion-weighting gradients $G_{dzs}$ in the current diffusion-weighting z-direction to excite reference transverse magnetization within two additional (reference) slice locations separated from the current parallel slices by ~0.25 of the imaging volume; the two additional (reference) slice locations are separated therebetween by 0.5-1 imaging volume (for example, by 14-28 slices of 28-slice volume). The two reference resonance-frequency ranges are determined by the magnitude of the additional diffusion-weighting gradients $G_{dzs}$, which technically may be applied as a continuation of the slice-selection gradient $G_s$. Based on the measured phase shift at the reference signal acquisition performed during maximum reference echo signal immediately before the balance RF pulse applying, said phase shift, which is dependent, particularly, on the bulk motion and deformation, is corrected by applying the compensation pulses. In a case of the phase shift more than $\pm\pi/2$ (90°) at the two-slice acquisition at spin-echo sequence unbalanced with respect to (the phase shift due to) first motion derivative, additional reference excitation and balance RF pulses may be applied during the diffusion-weighting gradients $G_{dz}$ applying as well. In the preferred embodiment of the two-slice SE-EPI, the reference signal phase shift is limited within $\pm\pi/2)(90°$ to prevent the slice misregistration between nodes due to the phase shift.

In this example, for faster reference signal relaxation, the flip angle of reference magnetization excitation is partial: $\alpha'=15-30°<60°$. Acquisition parameters included diffusion time $\Delta=25$ ms; repetition time $T_R=2$ s; the refocusing RF pulse shift 1-10 ms (that accordingly to Eq.(3) corresponds to detection flow rate corresponding to linear velocity 0.6 . . . 12 mm/s). By comparison of the mutually time-symmetrical unbalanced sequences with bulk motion and deformation compensation, perfusion in the current slice locations may be measured.

Thus, the found displacement and deformation in the diffusion-weighting direction during the combined diffusion time interval may be extrapolated to the period of SE-EPI readout for avoiding misregistration between the k-space nodes. Particularly, in the preferred embodiment of the two-slice DW MRI with the sequence unbalance with respect to the phase shift, the found deformation in the longitudinal diffusion-weighting direction may be used for amplitude correction of the slice-encoding gradient blips $B_s$ with a compensation blip (pulse) component for avoiding slice misregistration. In a case of a transversal diffusion-weighting direction, the found deformation and the bulk displacement in said direction may be used for amplitude correction of the phase-encoding gradient blips $B_p$ with a compensation blip (pulse) component and/or with uniform compensation blip component, for avoiding phase encode line misregistration. In the preferred embodiment of at least two reference excitation RF pulse applyings and correspondent number of additional reference echo signal acquisitions in single shot with a corresponding number of diffusion-weighting gradient pairs, more accurate extrapolation of displacement and deformation functions from to the period of SE-EPI readout may be achieved.

Figure 4:
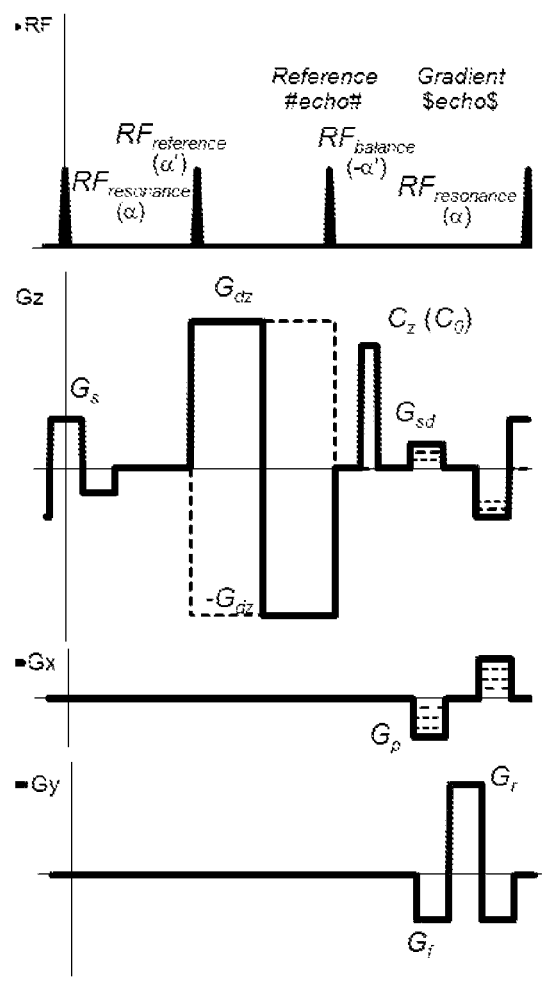
FIG. 4: A time diagram for performing the DW-MRI method according to the invention: an asymmetrical gradient-echo sequence (gradient lobes are applied time-symmetrically with respect to another sequence shown by the broken line)

A time diagram of an exemplary gradient-echo sequence unbalanced with respect to the first motion derivative with the partial-angle magnetization excitation in at least one current slice location, the reference magnetization excitation and balancing in the two additional reference slice locations, and the phase shift compensation is shown in FIG. 4. The dephasing diffusion-weighting gradients and the rephasing diffusion-weighting gradients having opposite polarity constitute the at least one bipolar diffusion-weighting gradient pulse pair $\pm G_{dz}$. The reference excitation and balancing RF pulses $RF_{reference}(\alpha')$, $RF_{balance}(-\alpha')$ are applied with a flipping angle at most equal to the flipping angle of the at least one excitation RF pulse $RF_{resonance}(\alpha)$: $\alpha=15°-30°>\alpha'$ (up to 60° providing necessary diffusion contrast in the steady state). Additional dephasing slice-selection gradient pair ±$G_{sd}$ is applied for focusing the gradient echo of the magnetization in the current slice location. The reference excitation resonance-frequency ranges are adjusted according to the diffusion-weighting gradients ±$G_{dz}$; the steady-state reference magnetization is being created in this embodiment. In another embodiment, the reference slice locations are being changed from cycle to cycle to provide for the returned reference magnetization enough time for relaxation (comparable with characteristic relaxation time $T_{1p}$) in each reference slice location.

The phase shift compensation pulses $C_z$, $C_0$ are applied after the balancing $RF_{balance}(\alpha')$ pulse during the reference echo duration and before the diffusion-weighted echo-signal acquisition during the steady-state gradient echo period duration. For perfusion-weighting sequence, acquisition parameters include low diffusion time Δ=2-10 ms; repetition time $T_R$=20-40 ms. Using diffusion-weighting sensitivity values as low as 50-500 s/mm², perfusion and fluid flow properties may be investigated.

In FIG. 3, shown by the broken line is the refocusing $RF''_{refocusing}(180°)$ pulse of a second unbalanced sequence shifted time-symmetrically with respect to $RF''_{refocusing}$ (180°) of a first sequence; the first and the second sequences are mutually symmetrically unbalanced with respect to the first motion derivative that may be used for detection of internal flow/perfusion by comparison of the opposite phase shifts in the imaging location. In FIG. 4, shown by the broken line is the bipolar diffusion-weighting gradient of a second sequence, the same by magnitude as one of a first sequence, the first and the second sequences having opposite bipolar gradient ±$G_{dz}$ direction; the first and the second sequences are mutually symmetrically unbalanced with respect to the first motion derivative that may be used for detection of internal flow/perfusion by comparison of the opposite phase shifts in the imaging location. The flow component of the signal phase shift (the flow derivative) is distinguished by determined reference phase shifts. The set of two sequences with opposite gradient polarity moments, one applied after another, allows the flow component to be canceled out and the steady-state diffusion/perfusion component of the echo signal may be characterized as a signal attenuation accrued during the steady-state signal formation. Thus, by comparison of two mutually time-symmetrical unbalanced sequences of the set (such as shown in FIG. 3 or in FIG. 4), perfusion in the current imaging locations may be measured after bulk motion and deformation compensation.

In another embodiment of the method, the set includes at least six sequences performed with diffusion-weighting gradient pairs applied in different diffusion-weighting directions to characterize a perfusion tensor; each sequence is performed with the refocusing RF pulse asymmetrically shifted with respect to the first and second diffusion-weighting gradient lobes of the diffusion-weighting gradient pair.

In another embodiment of the method, the set includes at least three sequences of RF and gradient pulses; one symmetrical sequence (i.e. with symmetrically applied refocusing RF pulse) for determining the diffusion component of the echo signal attenuation. At least two other sequences are asymmetrical (i.e. performed with the refocusing RF pulse mutually symmetrically shifted in opposite directions with respect to the first and second diffusion-weighting gradient lobes) for characterization of first and higher derivatives of flow and/or perfusion in the imaging location after the diffusion component elimination.

Figure 5:
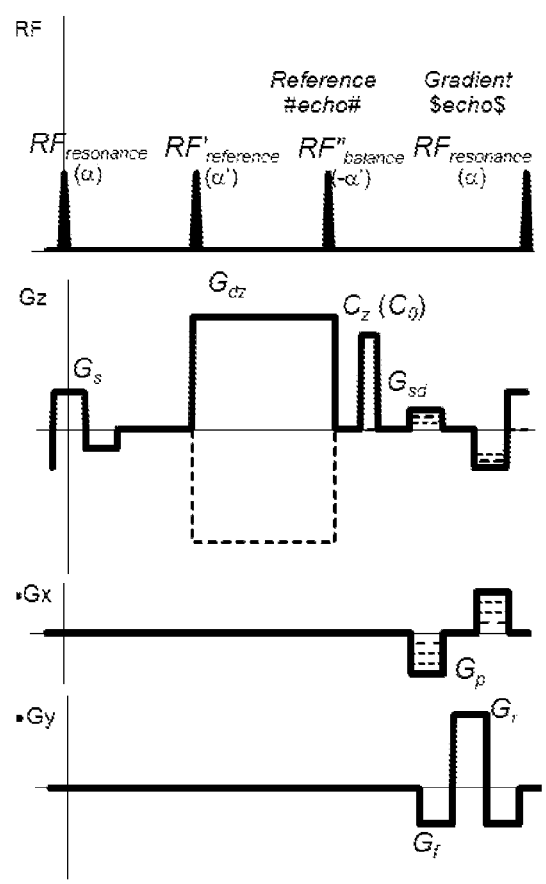
FIG. 5: A time diagram for performing the DW-MRI method according to the invention: a steady-state free precession sequence with cyclical drift having the unipolar diffusion-weighting gradient lobe (which, for another sequence, is applied symmetrically as shown by the broken line)

An exemplary time diagram for performing a steady-state sequence with cyclical drift having the unipolar diffusion-weighting gradient lobe is shown in FIG. 5. The unipolar diffusion-weighting gradient $G_d$ is applied about along the longitudinal direction in order to unbalance the sequence with respect to the first motion derivative. The unipolar diffusion-weighting gradients—$G_{dz}$ in another sequence may be applied with opposite sign, as shown by a broken line, at that the first and the second sequences are mutually symmetrically unbalanced with respect to the first motion derivative for detection of bulk motion at each stage. Sequential applying the sequences of the excitation RF pulse $RF_{resonance}$ and unipolar gradients ±$G_{dz}$, each sequence is unbalanced with respect to (the phase shift due to) first motion derivative, allows creation of a pathway for obtaining steady-state transversal magnetization with the steady-state gradient-echo signal as known from the art. The excitation RF pulse $RF_{resonance}(\alpha)$, preferably, α=20°-30° (flipping angle at α=α'=15°-60° generally supports steady-state magnetization) is applied with repetition time $T_R$=20-40 ms. The higher values of diffusion time (and the repetition time Δ=$T_R$) may be used for noise level decreasing and side effect mitigating. At that reference excitation pulse $RF'_{reference}(\alpha')$ with flipping angle α'<α may be applied for a motion-related phase shift compensation.

In the preferable embodiment of the steady-state DW-MRI method with cyclical drift, the pairs of reference excitation and balance RF pulses with flipping angle α'=α, $RF'_{reference}(\alpha')$, $RF'_{balance}(\alpha')$ are applied in the presence of the unipolar diffusion-weighting gradient $G_d$ at the start and at the finish of a pathway of the steady-state image creation; the reference phase shift is determined after the reference echo signal acquisition preceding the balancing RF pulse applying. The reference excitation pulses $RF'_{reference}(\alpha')$, $RF''_{reference}(\alpha')$ are applied each to excite, and, correspondingly, $RF'_{balance}(\alpha')$, $RF''_{balance}(\alpha')$—each to balance, the steady-state reference transverse magnetization within two additional (reference) slice locations separated from the current parallel slices by ~0.25 of the imaging volume; the two additional (reference) slice locations are separated therebetween by 0.5-1 imaging volume (for example, by 14-28 slices of 28-slice volume). In the embodiment with the balancing RF pulse applying, after acquiring the reference echo signal, the reference magnetization in said reference slice locations is being returned to the longitudinal direction by the balancing RF pulses. Based on the measured phase shifts of the reference signals and their gradient determined, particularly, by the bulk motion and deformation, the necessary compensation pulse parameters are calculated by the correction processor. Said phase shifts are corrected before the steady-state signal encoding and the gradient echo acquisition in each sequence by correspondent compensation pulses $C_z$, $C_0$ (or electronically in k-space directly by the correction processor). If the corrected phase shift is approaching to ±π (180°) then a few pairs of reference excitation and balance RF pulses may be applied during the applying of each unipolar diffusion-weighting gradient.

In the method embodiment, eliminating the measured phase shift due to the bulk motion and deformation may be used for comparing the drift-diffusion component with the diffusion/perfusion component. Assuming a proportional dependence between a fraction of fluid in the imaging location and a drift component of the signal attenuation, one can find the fraction of fluid by comparison of the measured drift component of the signal attenuation with drift attenuation at 100% fraction of the fluid found experimentally or theoretically. The drift component in the imaging location is governed by the longitudinal polarizing magnetic field coupling with the diffusion-weighting gradient in the longitudinal direction; the drift is absent at transversal diffusion-weighting directions. Distinguishing the drift component for determining the fraction of fluid and/or ADC is based on the comparison of the signal attenuation and/or of the phase shift at longitudinal diffusion-weighting direction with ones due to diffusion/perfusion measured at transversal diffusion-weighting directions.

In another embodiment, the steady-state DW-MRI method with cyclical drift may be used for determining the fluid fraction after eliminating the detected phase shift of the reference diffusion-weighted echo signals. The method comprises applying the excitation RF with partial flipping angles and the diffusion-weighting gradient being unipolar and applied along about longitudinal direction; a drift component of drift-diffusion and a fluid fraction in the imaging location are determined based on a the phase shift of the diffusion-weighted echo signal during the unipolar diffusion-weighting gradient applying. The drift component created by driving force of longitudinal diffusion-weighting gradient is distinguished by a comparison of the signal attenuations at longitudinal and transversal diffusion-weighting directions; and the fluid fraction is determined as a proportion factor between the determined drift component and one determined (theoretically or by reference measurement) for drift-diffusion at 100% fluid fraction.

In the steady-state cyclical drift sequence performing example with higher diffusion and repetition times $T_R=\Delta=35$ ms; uniform pulse duration $\delta=20$ ms; flipping angle $\alpha=30°$; diffusion-weighting gradient $G_{dz}=40$ mT/m, the drift component of the particle displacement and correspondingly attenuation at 100% fluid fraction in the imaging location becomes of order of the diffusion component (which is about 10 µm particle displacement at ADC in a lesion location about $1.6*10^{-9}$ m/s$^2$). At 0% fluid fraction, the drift component would be negligible. With the zero net phase shift of the transverse magnetization during sequence cycle pathway of creating the steady-state echo-signal, the drift component is being canceled out and the steady-state diffusion component is created (with the signal attenuation increased due to the drift component of a particle displacement accrued during the steady-state signal formation).

In the steady-state cyclical drift sequence embodiment providing sharper steady-state reference diffusion-/perfusion-weighted echo signal, more than one pair of reference excitation and balance RF pulses $RF'_{reference}(\alpha')$, $RF'_{balance}(\alpha')$ may be applied in the presence of the additional bipolar diffusion-weighting gradients $\pm G_{dzs}$ (first of which may be continuation of the slice-selection gradient $G_s$) applied along the current diffusion-weighting direction of the unipolar diffusion-weighting gradient $G_{dz}$.

Figure 6:
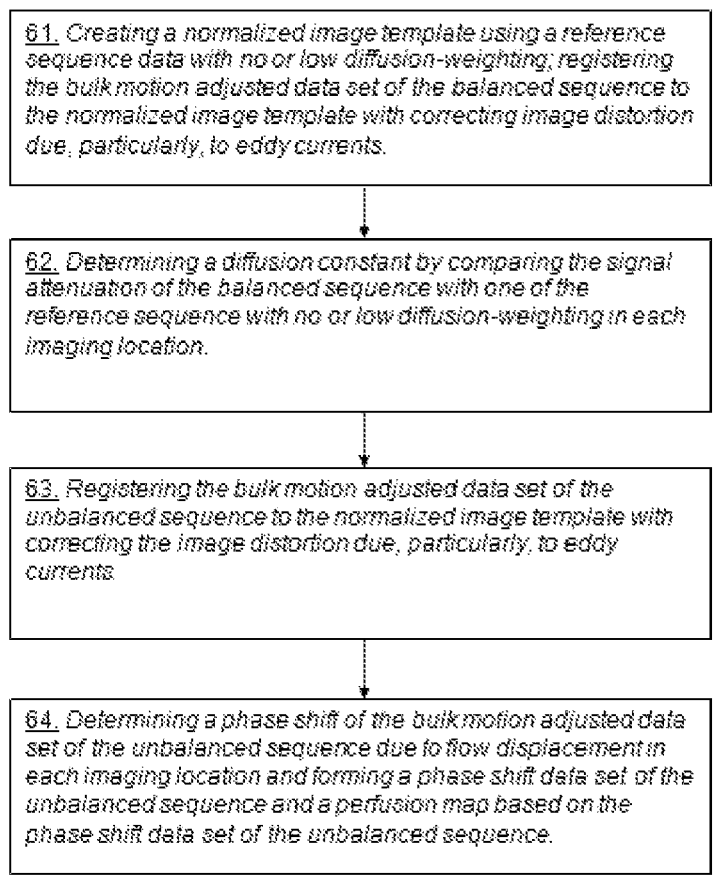
FIG. 6: A block diagram for illustrating the programmed processor algorithm serving to determine a flow/perfusion component based on the diffusion-weighted echo signal acquisitions of two sequences, symmetrical and asymmetrical.

A block diagram for illustrating the programmed processor algorithm serving to determine a perfusion component based on the diffusion-weighted echo signal acquisitions of two sequences, first symmetrical (balanced) and second asymmetrical (unbalanced with respect to the first motion derivative), is shown in FIG. 6. The echo signals of the symmetrical and asymmetrical sequences having the same diffusion-weighting direction were corrected according to the determined reference phase shift during the diffusion-weighting, bulk motion adjusted images thus obtained. The non-zero moment of the diffusion-weighting gradients of the asymmetrical sequence causes an additional phase shift due to flow in the imaging location, with phase shift magnitude not exceeding $\pi(180°)$.

In a balanced sequence data set registering stage 61, the $T_2$-weighted reference data set of a sequence with no or low diffusion-weighting is acquired and rigidly registered to a normalized (standardized) template. Subsequent registrations of each bulk-motion adjusted DW-MRI image to the normalized target volume will then cause entire DWI dataset to be positioned in a standardized orientation. Although this reference image volume is free from image distortions due to eddy currents, it contains geometrical distortions due to main magnetic field inhomogeneity, which are the same in DWI and thus do not cause misregistration artifacts. For the correction of the geometrical and brightness distortions due to eddy currents of the bulk motion adjusted balanced sequence data set, for example, a state-of-the-art correlation- and/or mutual information-based registration algorithm may be used, a warping function may be found to align each DWI volume in a dataset to a normalized template with interpolation of the images and optimal correction. After the registration, the image intensity and b-matrix of each voxel is adjusted according to the spatial transformation applied to it. Then a diffusion constant determining stage 62 may be performed based on Eqs.(1), (2). An unbalanced sequence data set registering stage 63 is decomposed into two steps. The first step includes correction of the geometrical and brightness distortion due to eddy currents of the bulk motion adjusted unbalanced sequence data set, for example, using the warping function found for the balanced image for each image location in the stage 61. The second step may include correction of the geometrical distortion due to flow/perfusion providing that corresponding phase shifts are small enough for automatic recognizing of said distortions. In a perfusion map forming stage 64, a phase shift due to flow displacement in each voxel corresponding to unbalanced sequence data set registered to the normalized template is determined; the perfusion map is determined based on Eq.(3).

Figure 7:
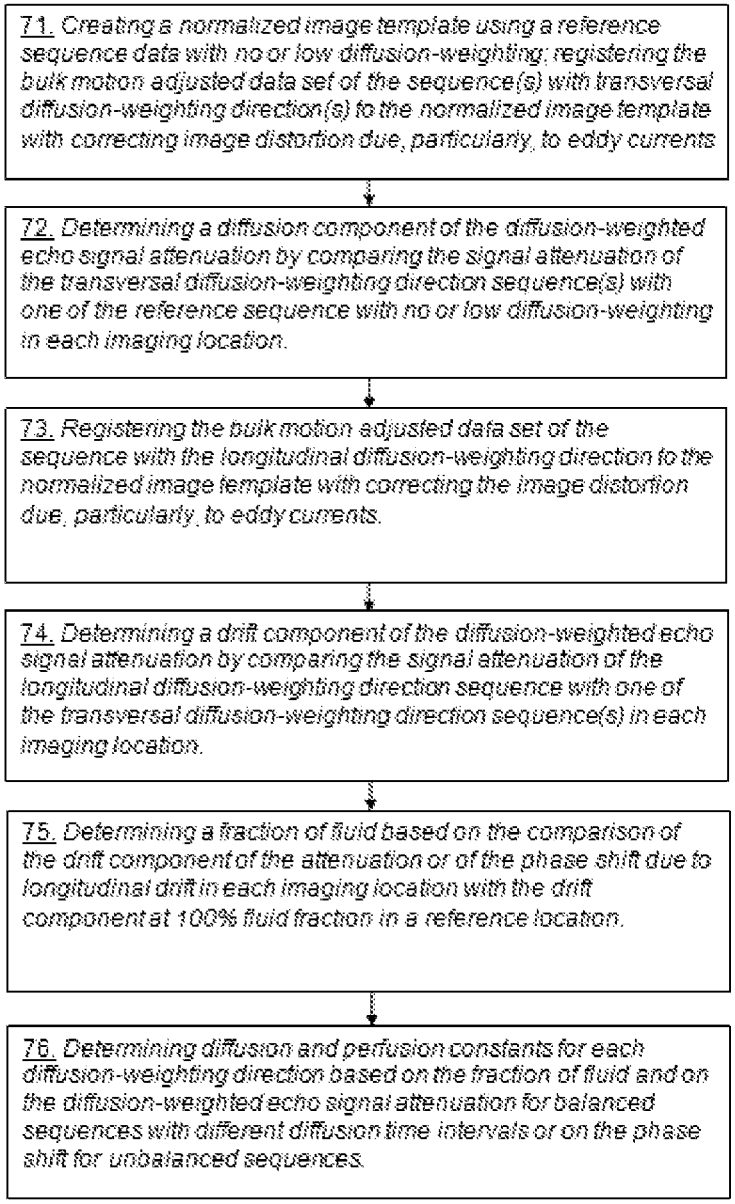
FIG. 7: A block diagram for illustrating the programmed processor algorithm serving to determine a fluid fraction based on a comparison of the diffusion-weighted echo signal acquisitions of two steady-state sequences, with longitudinal (asymmetrical) and transversal (symmetrical) diffusion-weighted directions.

A block diagram for illustrating the programmed processor algorithm serving to determine a fluid fraction based on a comparison of the diffusion-weighted echo signal acquisitions of two steady-state sequences having longitudinal and transversal diffusion-weighted directions for determining diffusion and perfusion matrices is shown in FIG. 7. The echo signals of both sequences were adjusted according to the determined reference phase shift during the diffusion-weighting and said two bulk motion adjusted data sets were obtained. Each asymmetrical (unbalanced) uniform diffusion-weighting gradient applying in the longitudinal direction causes longitudinal drift of the magnetization having longitudinal component, which is proportional to a mean diffusion path in a current voxel. While balanced at the finish of a pathway of the steady-state image creation, this drift increases the apparent diffusion coefficient (APD) at longitudinal diffusion-weighting direction. This increase, particularly, is proportional to a fluid fraction in the current voxel.

In a transversal diffusion-weighting direction sequence data set registering stage 71, the $T_2$-weighted reference data set of a sequence with no or low diffusion-weighting is acquired and rigidly registered to a normalized (standardized) template. Subsequent registrations of each bulk-motion adjusted DW-MRI image to the normalized target volume will then cause entire DWI dataset to be positioned in a standardized orientation and with correcting image distortions due, particularly, to eddy currents. A warping function may be found to align each DWI volume in a dataset to a normalized template with interpolation of the images and optimal correction of the geometrical and brightness distortion due to eddy currents. After the registration of a bulk motion adjusted data set of the steady-state sequence with transversal diffusion-weighting direction, in a diffusion component determining stage 72, the image intensity is adjusted according to the spatial transformation applied to it; a diffusion component of the diffusion-weighted echo-signal attenuation of the steady-state sequence with transversal diffusion-weighting direction is determined by comparison with the $T_2$-weighted reference data set. The APD distribution is preliminary determined based on Eqs.(1), (2). A longitudinal diffusion-weighting direction sequence data set registering stage 73 is decomposed into two steps. The first step includes correction of the geometrical and brightness distortion due to eddy currents of the bulk motion adjusted unbalanced sequence data set, for example, using the warping function found for the balanced image for each image location in the stage 71. The second step may include correction of the geometrical distortion due to longitudinal drift providing that corresponding phase shifts are small enough for automatic recognizing of said distortions. In a drift component determining stage 74, the drift component is determined by comparing signal attenuations of steady-state sequences with longitudinal and transversal diffusion-weighting directions in each imaging location. The phase shifts due to the longitudinal drift also may be used for determining the drift component. In a fluid fraction determining stage 75, the fluid fraction is determined by comparing the drift component with reference one with 100% fluid fraction. The reference drift component with 100% fluid fraction is determined theoretically based on state-of-the-art drift-diffusion modeling or experimentally at a reference imaging location with 100% fluid fraction. In a diffusion/perfusion constant determining stage 76, the diffusion and perfusion constants are determined accordingly to an equation system model based on Eq.(4) for the found fraction of fluid in each imaging location and attenuation matrices found for balanced sequences in each diffusion-weighting direction. Additionally, the phase shifts found for unbalanced sequences in each diffusion-weighting direction may be used. Balanced sequences with different diffusion time intervals and/or unbalanced for more sophisticated phase shift analysis may be used.

The MRI method of the invention may be adapted for use with a wide array of clinical applications including high-productivity whole-body scans, assessments of diffusion and perfusion properties and structure of biological tissue (characterization of brain structure, abdominal perfusion, cardiac muscle deformation, etc.), detection of lesions, tumor cell invasion, drug infusion monitoring, etc. Non-clinical applications may include ultra-fast low-field techniques, for example, used in airport security imaging systems. Diffusion-weighted nuclear magnetic characterization of samples performed with data acquisition from different sample locations (i.e. with nuclear MR imaging) may be performed, for example, for samples of hydrocarbon-bearing formation.

Uses stated above as well as additional uses and novel features of the invention set forth in part in the description and figures are intended to be for illustrative purposes only, and not intended in any way to limit the invention, in part become apparent to those skilled in the art on the description examination, or may be learned by practice of the invention.

The disclosed embodiments are merely exemplary of the invention, which may be embodied in various forms. Therefore, specific functional details disclosed herein are not interpreted as limiting, but merely as an illustrative basis for the claims and for teaching one skilled in the art to variously employ the present invention in any appropriate MRI system. While the description of the invention above enables one skilled in the art to make and use what is considered presently to be the best mode thereof, those skilled in the art will understand and appreciate the existence of variations, combinations, and equivalents of the specific embodiment, method, and examples herein. Although the particular embodiments of the invented method and apparatus for MRI are described, it is not intended that such description be construed as limiting the scope of this invention, except as set forth in the following claims.

What is claimed is:

1. A method for magnetic resonance imaging, wherein an imaging volume is subjected to at least one sequence of resonance frequency (RF) pulses and gradient magnetic field pulses (gradients), each RF pulse of the at least one sequence is applied in a presence of a gradient, the method comprising, in the at least one sequence:

applying at least one first excitation RF pulse within at least one first excitation resonance-frequency range in order to excite transverse magnetization within at least one first slice location within the imaging volume and in order to form at least one first echo signal from the first slice location;

applying at least one second excitation RF pulse within at least one second excitation resonance-frequency range in order to excite transverse magnetization within at least one second slice location within the imaging volume, the at least one second slice location is distinguished from the at least one first slice location, and in order to form, prior to the at least one first echo signal, at least one second echo signal from the at least one second slice location; and acquiring the at least one first and the at least one second echo signals in order to form a corrected data set, wherein, of the at least one first and the at least one second echo signals, at least one echo signal is formed with phase encoding, at least another echo signal is at least one reference echo signal; at least one phase shift of the at least one reference echo signal is at least one reference phase shift, a motion-related phase shift of the at least one echo signal is compensated based on the at least one reference phase shift.

2. The method of claim 1, wherein, the at least one first excitation RF pulse is applied in a presence of at least one first gradient; the at least one second excitation RF pulse is applied, after the at least one first excitation RF pulse, in a presence of at least one second gradient; the at least one reference echo signal is formed without phase encoding.

3. The method of claim 2, wherein the at least one second gradient is at least one diffusion-weighting gradient applied along at least one diffusion-weighting direction; the at least one second excitation RF pulse is at least one reference excitation RF pulse, which is applied within at least one reference excitation resonance-frequency range in a presence of the at least one diffusion-weighting gradient; the acquiring of the at least one second echo signal is performed in a presence of the at least one diffusion-weighting gradient in order to determine the reference phase shift; the acquiring of the at least one first echo signal is performed in a presence of at least one readout gradient in order to phase encode a location within the first slice location.

4. The method of claim 3, wherein at least one balancing RF pulse is additionally applied in a presence of the at least one diffusion-weighting gradient in order to balance transverse magnetization within the at least one second slice location after the acquiring of the at least one reference echo signal and prior to the acquiring of the at least one first echo signal.

5. The method of claim 3, wherein the at least one reference excitation RF pulse is applied within at least two reference excitation resonance-frequency ranges; the at least one reference echo signal from the at least one second slice location is at least two reference echo signals from at least two second slice locations; the at least one reference phase shift is at least two reference phase shifts; a gradient of the at least two reference phase shifts with respect to the at least one diffusion-weighting direction is determined in order to characterize deformation along the at least one diffusion-weighting direction.

6. The method of claim 5, wherein at least one compensation sufficiently uniform magnetic field pulse dimensioned to compensate the at least one motion-related phase shift and/or at least one compensation gradient magnetic field pulse dimensioned to compensate the gradient of the at least two phase shifts with respect to the at least one diffusion-weighting gradient direction are applied prior to the acquiring of the at least one first echo signal.

7. The method of claim 3, wherein the at least one diffusion-weighting gradient comprises at least one pair of diffusion-weighting gradients having same polarity; a refocusing RF pulse is applied about symmetrically between diffusion-weighting gradients of the at least one pair in order to form a symmetrical diffusion-weighted sequence, which is characterized by a first derivative of the at least one reference phase shift being about compensated, in order to characterize transverse magnetization diffusion in the at least one first slice location.

8. The method of claim 3, wherein the at least one diffusion-weighting gradient comprises at least one pair of diffusion-weighting gradients having same polarity; a refocusing RF pulse is applied with asymmetrical shift between diffusion-weighting gradients of the at least one pair in order to form an asymmetrical diffusion-weighted sequence, which is characterized by a first derivative of the at least one reference phase shift being uncompensated, in order to characterize flow and/or perfusion in the at least one first slice location.

9. The method of claim 3, wherein the at least one diffusion-weighting gradient comprises at least one pair of diffusion-weighting gradients having opposite polarities in order to form an asymmetrical diffusion-weighted sequence, which is characterized by a first derivative of the at least one reference phase shift being uncompensated, in order to characterize flow and/or perfusion in the at least one first slice location.

10. The method of claim 3, wherein the at least one first excitation RF pulse and the at least one reference excitation RF pulse are applied with a partial flipping angle 15-60°, preferably 20-30°; the at least one reference excitation RF pulse is applied with a flipping angle at most equal to the flipping angle of the at least one first excitation RF pulse; the at least one diffusion-weighting gradient is a unipolar diffusion-weighting gradient; the at least one diffusion-weighting direction is about the magnetic field direction in order to form an asymmetrical diffusion-weighted sequence, which is characterized by a first derivative of the at least one reference phase shift being uncompensated, in order to characterize a transverse magnetization drift along the magnetic field direction in the at least one first slice location.

11. A method for magnetic resonance imaging, wherein an imaging volume is subjected to at least one first and at least one second diffusion-weighted sequences of resonance frequency (RF) pulses and gradient magnetic field pulses (gradients), in order to form, correspondingly, a first and a second corrected data sets, the method comprising, in each of the at least one first and the at least one second diffusion-weighted sequences,
applying at least one first excitation RF pulse within at least one first excitation resonance-frequency range in a presence of a slice-selection gradient in order to excite transverse magnetization within the at least one first slice location within the imaging volume and to in order form at least one first echo signal from the at least one first slice location;
applying, after the at least one first excitation RF pulse, at least one reference excitation RF pulse within at least one second excitation resonance-frequency range in a presence of at least one diffusion-weighted gradient in order to excite transverse magnetization within at least one second slice location within the imaging volume, the at least one second slice location is distinguished from the at least one first slice location, and in order to form, prior to the at least one first echo signal, at least one reference echo signal from the at least one second slice location; and
acquiring the at least one first echo signal with phase encoding and the at least one second echo signal without phase encoding, at least one phase shift of the at least one reference echo signal, which is the at least one second echo signal, is at least one reference phase shift, the at least one reference phase shift is determined in order to compensate a motion-related phase shift of the at least one first echo signal,
wherein, the second diffusion-weighted sequence is asymmetrical, which is characterized by a first derivative of the at least one reference phase shift being uncompensated, the at least one reference phase shift of the at least one first diffusion-weighted sequence is being sufficiently distinguished from the at least one reference phase shift of the at least one second diffusion-weighted sequence in order to distinguish a flow and/or perfusion component from a diffusion component of transverse magnetization decay in the first slice location based on a comparison of the first and the second corrected data sets.

12. The method of claim 11, wherein the first diffusion-weighted sequence and the second diffusion-weighted sequence are both asymmetrical and characterized by the reference phase shifts of said first and second sequences being mutually opposite.

13. The method of claim 11, wherein the first diffusion-weighted sequence is about symmetrical, which is characterized by a first derivative of the at least one reference phase shift being about compensated, in order to characterize the diffusion component of the transverse magnetization decay in the first slice location; the second diffusion-weighted sequence comprises at least six asymmetrical sequences having different diffusion-weighting directions in order to characterize a perfusion tensor in the first slice location after eliminating the diffusion component.

14. The method of claim 11, wherein, in each of the first and the second diffusion-weighted sequences, the at least one first excitation RF pulse is applied with a partial flipping angle being at most 60°, the diffusion-weighting gradient is unipolar, wherein, the unipolar diffusion-weighting gradient of the first diffusion-weighted sequence is applied about along the direction transversal to the magnetic field; the unipolar diffusion-weighting gradient of the second diffusion-weighted sequence is applied about along the magnetic field direction to distinguish drift component of transverse magnetization decay in the first slice location, in order to characterize a transverse magnetization drift and/or a fraction of fluid.

15. An apparatus for magnetic resonance imaging comprising:
a resonance frequency (RF) coil means and a gradient magnetic coil means in order to subject an imaging volume to a sequence of RF pulses and gradient magnetic field pulses (gradients), each RF pulse of the sequence is applied in a presence of a gradient;

a RF coil control means and a magnetic coil control means in order to apply at least one first excitation RF pulse within at least one first excitation resonance-frequency range, for exciting transverse magnetization within the at least one first slice location within the imaging volume and for forming at least one first echo signal from the at least one first slice location, and in order to apply at least one second excitation RF pulse within at least one second excitation resonance-frequency range, for exciting transverse magnetization within at least one second slice location within the imaging volume, the at least one second slice location is distinguished from the at least one first slice location, and for forming, prior to the at least one first echo signal, at least one second echo signal from the at least one second slice location;

a receiver means in order to acquire the at least one first and the at least one second echo signals in order to form a corrected data set, the receiver means is adjusted to acquire, of the at least one first and the at least one second echo signals, at least one echo signal with phase encoding, wherein, at least another echo signal is at least one reference echo signal, at least one phase shift of the at least one reference echo signal is at least one reference phase shift; and a processor means in order to compensate a motion-related phase shift of the at least one echo signal based on the at least one reference phase shift.

16. The apparatus of claim 15, wherein the RF coil control means is additionally adjusted to apply the at least one first excitation RF pulse in a presence of at least one first gradient and to apply, after the at least one first excitation RF pulse, the at least one second excitation RF pulse in a presence of at least one second gradient; the receiver means is additionally adjusted to acquire the at least one reference echo signal without phase encoding.

17. The apparatus of claim 16, wherein the magnetic coil control means is additionally adjusted to apply at least one second gradient, which is at least one diffusion-weighting gradient applied along at least one diffusion-weighting direction; the RF coil control means is additionally adjusted to apply the at least one second excitation RF pulse, which is the at least one reference excitation RF pulse applied within at least one reference excitation resonance-frequency range, in a presence of the at least one diffusion-weighting gradient; the receiver means is additionally adjusted to acquire the at least one second echo signal in a presence of the at least one diffusion-weighting gradient in order to determine the reference phase shift and to acquire the at least one first echo signal in a presence of at least one readout gradient in order to phase encode a location within the first slice location.

18. The apparatus of claim 17, wherein, the RF coil control means is additionally adjusted to apply at least one balancing RF pulse in a presence of the at least one diffusion-weighting gradient in order to balance transverse magnetization within the at least one second slice location after the acquiring of the at least one reference echo signal and prior to the acquiring of the at least one first echo signal.

19. The apparatus of claim 17, wherein the RF coil control means is additionally adjusted to apply the at least one reference excitation RF pulse within at least two reference excitation resonance-frequency ranges, the at least one reference echo signal from at least one second slice location is at least two reference echo signals from at least two second slice locations, the at least one reference phase shift is at least two reference phase shifts; and the processor means is additionally programmed to determine a gradient of the at least two reference phase shifts with respect to the at least one diffusion-weighting direction in order to characterize deformation along the at least one diffusion-weighting direction.

20. The apparatus of claim 19, additionally comprising the uniform magnetic coil means in order to apply, prior to the acquiring of the at least one first echo signal, at least one compensation sufficiently uniform magnetic field pulse dimensioned to compensate the at least one reference phase shift; and/or the magnetic coil control means is additionally adjusted in order to apply, prior to the acquiring of the at least one first echo signal, at least one compensation gradient magnetic field pulse dimensioned to compensate the gradient of the at least two phase shifts with respect to the at least one diffusion-weighting gradient direction.

* * * * *